(12) United States Patent
Melvin

(10) Patent No.: US 6,520,904 B1
(45) Date of Patent: Feb. 18, 2003

(54) DEVICE AND METHOD FOR RESTRUCTURING HEART CHAMBER GEOMETRY

(75) Inventor: David B. Melvin, Loveland, OH (US)

(73) Assignee: The University of Cincinnati, Cincinnati, OH (US)

( * ) Notice: Subject to any disclaimer, the term of this patent is extended or adjusted under 35 U.S.C. 154(b) by 0 days.

(21) Appl. No.: 09/326,416

(22) Filed: Jun. 4, 1999

Related U.S. Application Data

(63) Continuation-in-part of application No. 09/316,611, filed on May 21, 1999, now abandoned, which is a continuation-in-part of application No. 09/165,887, filed on Sep. 30, 1998, now Pat. No. 6,221,103, which is a continuation-in-part of application No. 08/581,914, filed on Jan. 2, 1996, now Pat. No. 5,957,977.

(51) Int. Cl.⁷ ............................... A61F 1/00; A61F 2/24
(52) U.S. Cl. ......................................... 600/16; 623/3.1
(58) Field of Search .................. 600/16, 17, 18, 600/37; 601/151–153; 607/126; 623/3.1, 2.36, 2.37, 2.38, 11.11

(56) References Cited

U.S. PATENT DOCUMENTS

| | | |
|---|---|---|
| 2,826,193 A | 3/1958 | Vineberg |
| 3,053,249 A | 9/1962 | Smith |
| 3,455,298 A | 7/1969 | Anstadt |
| 3,513,836 A | 5/1970 | Sausse |
| 3,590,815 A | 7/1971 | Schiff |
| 3,613,672 A | 10/1971 | Schiff |
| 3,668,708 A | 6/1972 | Tindal |
| 3,713,439 A | 1/1973 | Cabezudo |
| 3,791,388 A | 2/1974 | Hunter et al. |
| 3,827,426 A | 8/1974 | Page et al. |
| 3,983,863 A | 10/1976 | Janke et al. |
| 4,192,293 A | 3/1980 | Asrican |
| 4,536,893 A | 8/1985 | Parravicini |
| 4,621,617 A | 11/1986 | Sharma |
| 4,690,134 A | 9/1987 | Snyders |

(List continued on next page.)

FOREIGN PATENT DOCUMENTS

| | | |
|---|---|---|
| EP | 119357 | 9/1984 |
| EP | 0583012 | 2/1988 |
| SU | 1191-076 A | 11/1985 |
| WO | WO9829041 | 7/1998 |
| WO | WO 99/30647 | 6/1999 |
| WO | WO 99/53977 | 10/1999 |
| WO | WO 00/02500 | 1/2000 |
| WO | WO 00/06026 | 2/2000 |
| WO | WO 00/06027 | 2/2000 |
| WO | WO 00/06028 | 2/2000 |
| WO | WO 00/16700 | 3/2000 |

OTHER PUBLICATIONS

Tellides et al, *Journal of Heart and Lung Transplantation*, (1998)17:1, Abstract No. 180, p. 89.
Kawaguchi et al, *Journal of Heart and Lung Transplantation*, (1998)17:1, Abstract No. 181, p. 89.
Dowling et al, *Journal of Heart and Lung Transplantation*, (1998)17:1, Abstract No. 76, p. 62.
Khoynezhad et al, *Journal of Heart and Lung Transplantation*, (1998)17:1, Abstract No. 77, p. 62.
Batista et al, *Ann. Thorac. Surg.*, (1977)64, p. 634–638.

(List continued on next page.)

*Primary Examiner*—David J. Isabella
(74) *Attorney, Agent, or Firm*—Ratner & Prestia

(57) ABSTRACT

A geometric reconfiguration assembly for the natural heart having a collar configured for surrounding the natural heart. The collar can include a plurality of supports configured for positioning on the epicardial surface of the heart. Supports can be joined with connectors that can permit or provide slight deformation of the assembly. An external shell or skin portion can be provided around the supports an/or connectors.

27 Claims, 19 Drawing Sheets

U.S. PATENT DOCUMENTS

| | | |
|---|---|---|
| 4,809,676 A | 3/1989 | Freeman |
| 4,846,831 A | 7/1989 | Skillin |
| 4,904,255 A | 2/1990 | Chareire et al. |
| 4,936,857 A | 6/1990 | Kulik |
| 4,957,477 A | 9/1990 | Lundback |
| 5,109,843 A | 5/1992 | Melvin et al. |
| 5,119,804 A | 6/1992 | Anstadt |
| 5,131,905 A | 7/1992 | Grooters |
| 5,139,517 A | 8/1992 | Corral |
| 5,169,381 A | 12/1992 | Snyders |
| 5,192,314 A | 3/1993 | Daskalakis |
| 5,201,880 A | 4/1993 | Wright et al. |
| 5,256,132 A | 10/1993 | Snyders |
| 5,258,021 A | 11/1993 | Duran |
| 5,334,217 A | 8/1994 | Das |
| 5,345,949 A | 9/1994 | Shlain |
| 5,358,519 A | 10/1994 | Grandjean |
| 5,370,685 A | 12/1994 | Stevens |
| 5,383,840 A | 1/1995 | Heilman et al. |
| 5,385,528 A | 1/1995 | Wilk |
| 5,484,391 A | 1/1996 | Buckman, Jr. et al. |
| 5,487,760 A | 1/1996 | Villafana |
| 5,533,958 A | 7/1996 | Wilk |
| 5,571,176 A | 11/1996 | Taheri |
| 5,593,424 A | 1/1997 | Northrup, III |
| 5,655,548 A | 8/1997 | Nelson et al. |
| 5,702,343 A | 12/1997 | Alferness |
| 5,709,695 A | 1/1998 | Northrup, III |
| 5,713,954 A | 2/1998 | Rosenberg et al. |
| 5,738,626 A | 4/1998 | Jarvik |
| 5,738,627 A | 4/1998 | Kovacs et al. |
| 5,749,883 A | 5/1998 | Halpern |
| 5,800,528 A | 9/1998 | Lederman et al. |
| 5,824,071 A | 10/1998 | Nelson et al. |
| 5,910,124 A | 6/1999 | Rubin |
| 5,957,977 A * | 9/1999 | Melvin ..................... 623/3.1 |
| 5,961,440 A | 10/1999 | Schweich, Jr. et al. |
| 6,019,722 A | 2/2000 | Spence et al. |
| 6,045,497 A | 4/2000 | Schweich, Jr. et al. |
| 6,050,936 A | 4/2000 | Schweich, Jr. et al. |
| 6,059,715 A | 5/2000 | Schweich, Jr. et al. |
| 6,077,214 A | 6/2000 | Mortier et al. |
| 6,179,791 B1 | 1/2001 | Krueger |
| 6,183,411 B1 | 2/2001 | Mortier et al. |

OTHER PUBLICATIONS

Melvin, D.B.; Conkle, D.; Roberts, A., Stinson, E.; "Cardiac Performance and Myocardial Contractility after Experimenal Mechancial Ventricular Assistance" *J. Thoracic and Cardiovascular Surgery;* vol. 65, No. 6, Jun., 1973.

Melvin, D.B. "Cardiovascular Surgery; Myocardial Preservation, Cardiorespiratory Support I" *American Heart Association Abstract;* Circulation Part II, vol. 68, No. :4; Scientific Sessions for Nurses 37th Annual Meeting held on Nov. 14–17, 1983; (Poster) Oct., 1983.

Melvin, D.B.; Shamraj, O.; Grupp, I.; Grupp, G.; Gradoux, N.; Kremers, W.; Lingrel, J.; DePover, A.; Characterisation of Na/K–ATPase, its Isoforms, and the Intropic Response to Ouabain in Isolated Failing Human Hearts; *Cardiovas. Res.* vol. 27, No. 12, 1993.

Melvin, D.; Schima, H.; Losert, U.; Wolner, E.; Long–Term Ventricular Wall Actuation: Can and Should it be Systematically Explored? *Artificial Organs,* vol. 20, No. 1, 1996.

Melvin, D.B.; Schima, H.; Losert, U.; Stohr, H.; Siegl, H.; Huber, L.; Glos, D.; Wolner, E.; "A Physical Analog of the Failing Left Ventricle for In Vitro Studies of Mechanical Wall Actuation." *Artificial Organs;* vol. 20, No. 3, 1996.

Melvin, D.B. "Ventricular Radius Reduction Without Resection: A Computational Assessment," *ASAIO Journal (Abstract),* vol. 44, No. 2, pp. 57A, Mar. 5, 1998.

Melvin, D.B. "Ventricular Radius Reduction Without Resection: A Computational Assessment," *ASAIO Annual Meeting* (Poster), Jun., 1998.

Melvin, D.B.; Melvin, A.J.; Trossman, C.A.; Glos, D.L.; "Reduction of Ventricular Wall Tensile Stress by Geometric Remodeling Device," *ASAIO Journal* (Abstract), vol. 45, No. 2, pp. 166, Mar. 17, 1999.

Melvin, D.B.; Melvin, A.J.; Trossman, C.A.; Glos, D.L.; "Reduction of Venticular Wall Tensile Stress by Geometric Remodeling Device," *ASAIO Annual Meeting* (Poster), Jun., 1999.

Melvin, D.B., "Ventricular Radius Reduction Without Resection: A Computational Analysis," *ASAIO Journal,* vol. 45, No. 3, May–Jun., 1999.

Boyer, Mike, "Shortcut to Innovation. SDRC Agreement Could Hasten Medical Advances," *The Cininnati Enquirer,* Mar. 2, 1999.

Miller, Nick, "SDRC Gives its Software to BIO/START," *The Cincinnati Post,* Mar. 2, 1999.

Bonfield, Tim, "CardioClasp may help Biomedicals," *The Cincinnati Enquirer,* Nov. 7, 1999.

Bonfield, Tim, "Surgeon's Invention Could Help Thousands," *The Cincinnati Enquirer,* Nov. 7, 1999.

Vacariello, Linda, "Who Will Invent the Cures?" *Cincinnat,* Dec. 1999, p. 64.

Melvin, D.B., "Device–Induced Ventricular Geometric Remodeling: Appraisal of Critical Issues," *Journal of Cardiac Surgery,* (Accepted for publication). Presented at the 3rd symposium of the Society of Cardiac Volume Reduction, Apr. 9, 2000 in Osaka, Japan).

Shimizu, J., et al., "A Passive Device to Improve Systolic Performance in Experimental heart Failure in Canines," *HFSA Annual Meeting* (Poster), Sep., 2000.

Shimizu, J., et al., "Improved Systolic Performance by Passive Remodeling in Experimental Heart Failure," *American Heart Association Meeting (Paper) Circulation* Suppl II; vol. 102, No. 18, Nov., 2000.

Stewart, Mary, "Geometric Remodeling takes CHF Patients Back a Class," *Start–Up,* Jul./Aug., 2000.

* cited by examiner

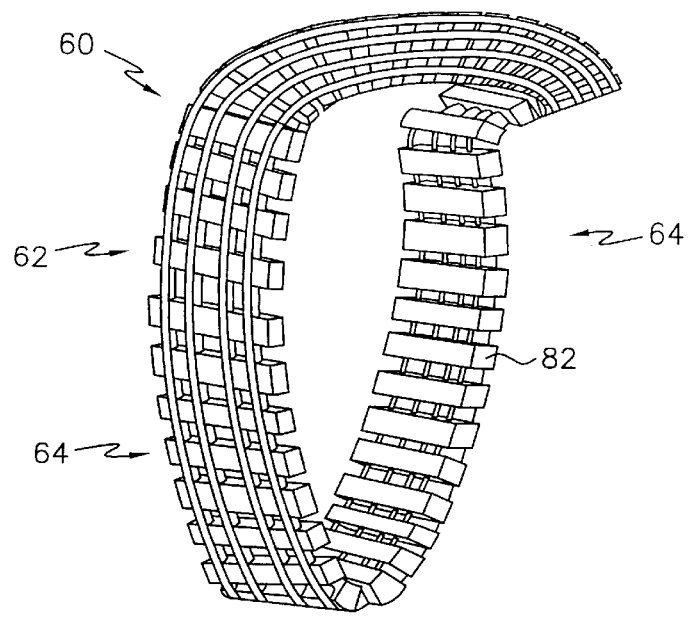
FIG. 5
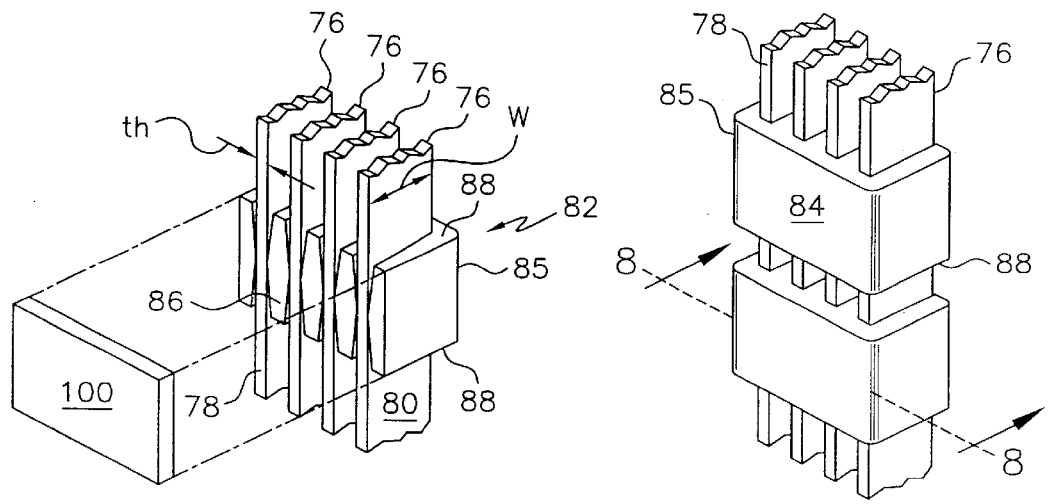
FIG. 6  FIG. 7

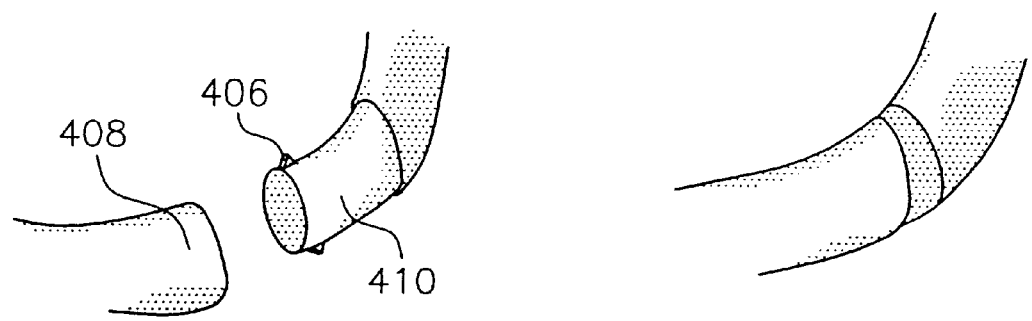
FIG. 27A
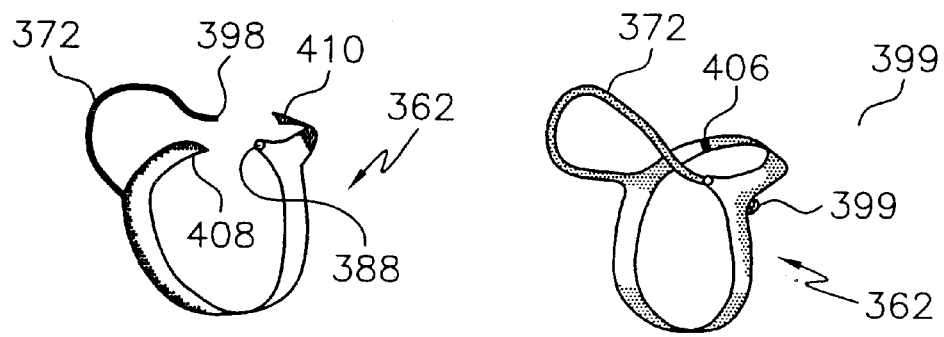
FIG. 27B  FIG. 27C
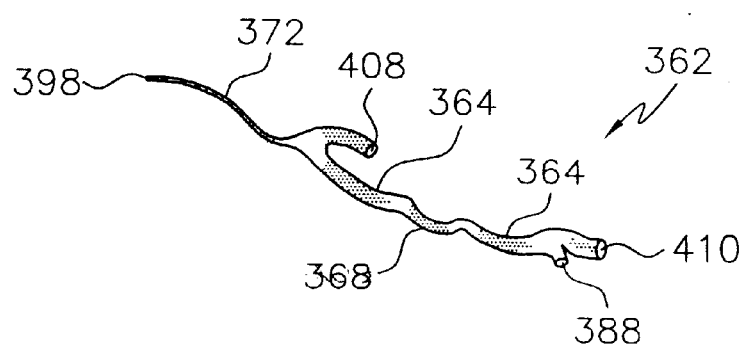
FIG. 27D

DEVICE AND METHOD FOR RESTRUCTURING HEART CHAMBER GEOMETRY

REFERENCE TO COPENDING APPLICATION

This is a continuation in part application of U.S. patent application Ser. No. 09/316,611, filed May 21, 1999 now abandoned (incorporated herein by reference), entitled "Device and Method for Restructuring Heart Chamber Geometry", which is a continuation in part application of U.S. patent application Ser. No. 09/165,887, filed Sep. 30, 1998 now U.S. Pat. No. 6,221,103 (incorporated herein by reference) entitled "Device and Method for Restructuring Heart Chamber Geometry", which is a continuation in part application of U.S. patent application Ser. No. 08/581,914, filed Jan. 2, 1996, now U.S. Pat. No. 5,957,977 (incorporated herein by reference), entitled "Activation Device for the Natural Heart and Method of Doing The Same".

TECHNICAL FIELD OF THE INVENTION

The present invention relates to devices and methods for treating cardiomyopathies and/or enlarged hearts and, more specifically, devices and methods for decreasing a-heart chamber's wall tension.

BACKGROUND OF THE INVENTION

The natural heart, and specifically, the cardiac muscle tissue of the natural heart (e.g., myocardium) can fail for various reasons to a point where the natural heart cannot provide sufficient circulation of blood for a body so that life can be maintained. More specifically, the heart and its chambers can become enlarged for a variety of causes and/or reasons, including viral disease, idiopathic disease, valvular disease (mitral, aortic and/or both), ischemic disease, Chagas' disease and so forth. As the heart and its chambers enlarge, tension of the walls of the heart's chambers increase and thus, the heart must develop more wall tensile stress to generate the needed pressure for pumping blood through the circulatory system. The process of ventricular dilation is generally the result of chronic volume overload or specific damage to the myocardium. In a normal heart that is exposed to long-term increased cardiac output requirements, for example, that for an athlete, there is an adaptive process of slight ventricular dilation and muscle myocyte hypertrophy. In this way, the heart may fully compensate for the increase cardiac output requirements of the body. With damage to myocardium or chronic volume overload, however, there are increased requirements put on the contracting myocardium to such a level that this compensated state is never achieved and the heart continues to dilate.

A problem with an untreated dilated ventricle is that there is a significant increase in wall tension and/or stress, both during the diastolic filling, and during the systolic contraction. In a normal heart, the adaption of muscle hypertrophy (e.g. thickening) in the ventricular dilation maintains a fairly constant wall tension for systolic constriction. However, in a failing heart, the ongoing dilation is greater than the hypertrophy, and as a result, rising wall tension is required for systolic contraction. This is believed to result in further muscle damage.

The increase in wall stress is also true for diastolic filling. Additionally, because of the lack of cardiac output, ventricular filling pressure tends to rise due to several physiologic mechanisms. Moreover, in diastole, both the diameter and wall pressure increase over normal levels, thus contributing to higher wall stress levels. As a solution for the enlarged natural heart, attempts have been made in the past to provide a treatment to maintain circulation. Prior treatments for heart failure generally fall into three categories, namely surgical treatments; mechanical support systems; or pharmacological.

One such approach has been to replace the existing natural heart in a patient with an artificial heart or a ventricular assist device. In using artificial hearts and/or assist devices, a particular problem stems from the fact that the materials used for the interior lining of the chambers of an artificial heart are in direct contact with the circulating blood, which can enhance undesirable clotting of the blood, build up of calcium, or otherwise inhibit the blood's normal function. Hence, thromboembolism and hemolysis could occur with greater ease. Additionally, the lining of an artificial heart or a ventricular assist device can crack, which inhibits performance, even if the crack is at a microscopic level. Moreover, these devices must be powered by a source which can be cumbersome and/or external to the body. Drawbacks have limited use of these devices to applications having too brief a time period to provide a real lasting benefit.

An alternative procedure is to transplant a heart from another human or animal into a patient. The transplant procedure requires removing an existing organ (i.e., the natural heart) for substitution with another organ (i.e., another natural heart) from another human, or potentially, from an animal. Before replacing an existing organ with another, the substitute organ must be "matched" to the recipient, which can be, at best, difficult and time consuming to accomplish. Furthermore, even if the transplanted organ matches the recipient, a risk exists that the recipient's body will reject the transplanted organ and attack it as a foreign object. Moreover, the number of potential donor hearts is far less than the number of patients in need of a transplant. Although use of animal hearts would lessen the problem with fewer donors than recipients, there is an enhanced concern with rejection of the animal heart.

In an effort to use the existing natural heart of a patient, other attempts have been made to reduce wall tension of the heart by removing a portion of the heart wall, such as a portion of the left ventricle in a partial left ventriculectomy procedure (the Batista procedure). A wedgeshaped portion of the ventricular muscle has been removed, which extends from the apex to the base of the heart. By reducing the chamber's volume, and thus its radius, the tension of the chamber's wall is reduced as well. There are, however, several drawbacks with such a procedure. First, a valve (i.e., the mitral valve) may need to be repaired or replaced depending on the amount of cardiac muscle tissue to be removed. Second, the procedure is invasive and traumatic to the patient. As such, blood loss and bleeding can be substantial during and after the procedure. Moreover, as can be appreciated by those skilled in the industry, the procedure is not reversible. Another device developed for use with an existing heart for sustaining the circulatory function of a living being and the pumping action of the natural heart is an external bypass system, such as a cardiopulmonary (heart-lung) machine. Typically, bypass systems of this type are complex and large, and, as such, are limited to short term use in an operating room during surgery, or to maintaining the circulation of a patient while awaiting receipt of a transplant heart. The size and complexity effectively prohibit use of bypass systems as a long term solution, as they are rarely even portable devices. Furthermore, long term use of these systems can damage the blood cells and blood borne products, resulting in post surgical complications such as bleeding, thromboembolism function, and increased risk of infection.

Medicines have been used to assist in treating cardiomyopathies. Some inotropic agents can stimulate cardiac work. For example, digoxin can increase the contractibility of the heart, and thereby enhances emptying of the chambers during systolic pumping. Medicines, such as diuretics or vasodilators attempt to reduce or decrease the heart's workload. For example, indirect vasodilators, such as angiotensin-converting enzyme inhibitors (e.g., enalopril), can help reduce the tendency of the heart to dilate under the increased diastolic pressure experienced when the contractibility of the heart muscle decreases. Many of these medicines have side effects, such as excessive lowering of blood pressure, which make them undesirable for long term therapy.

As can be seen, currently available treatments, procedures, medicines, and devices for treating end-stage cardiomyopathies have a number of shortcomings that contribute to the complexity of the procedure or device. The current procedures and therapies can be extremely invasive, only provide a benefit for a brief period of time, or have undesirable side effects which can hamper the heart's effectiveness. There exists a need in the industry for a device and procedure that can use the existing heart to provide a practical, long-term therapy to reduce wall tension of the heart, and thus improve its pumping efficiency.

SUMMARY OF THE PRESENT INVENTION

It is the object of the present invention to provide a device and method for treating cardiomyopathies that address and overcome the above-mentioned problems and shortcomings in the thoracic medicine art.

It is another object of the present invention to provide a device and method for treating cardiomyopathies that minimize damage to the coronary circulatory and the endocardium.

It is still a further another object of the present invention to provide a device and method for treating cardiomyopathies that maintain the stroke volume of the heart.

Another object of the present invention is to provide a device and method for treating cardiomyopathies that support and maintain the competence of the heart valves so that the heart valves can function as intended.

Still another object of the present invention is to provide a device and method that increase the pumping effectiveness of the heart.

Yet another object of the present invention is to provide a device and method for treating cardiomyopathies on a long term basis.

It is yet still an object of the present invention to provide a device and method for treating cardiomyopathies that do not require removal of any portion of an existing natural heart.

Still a further object of the present invention is to provide a device and method for treating dilated cardiomyopathies that directly reduce the effective radius of a chamber of a heart in systole as well as in diastole.

Additional objects, advantages, and other features of the present invention will be set forth and will become apparent to those skilled in the art upon examination of the following, or may be learned with practice of the invention.

To achieve the foregoing, a geometric reconfiguration assembly is provided for the natural heart having a collar configured for surrounding the natural heart. The collar can include a plurality of bands, such as thin bands of about 0.2 mm in thickness, in a spaced relationship to each other, and a connector bar intersecting the plurality of bands and configured for maintaining the spaced relationship of the bands to each other. The collar may include a plurality of bands, such as from about 2 to about 10 bands, that are positioned parallel to each other. The bands can each be made of a biomedical material, such as polyacetal or a metal, such as titanium or steel.

The connector bar of the present invention can be positioned tangential to the plurality of bands, and may have a plurality of grooves configured to receive the thickness of each of the plurality of bands. The grooves also may be beveled to allow for the bands to flex as the heart beats. The connector bar's inner surface can have an outwardly convex curved configuration, and may even include a cushioned portion that can be made from a polymeric material. A pad may be positioned between the collar and the epicardial surface of the heart that may comprise a low durometer polymer, or either a gel-filled cushion or a fluid-filled cushion.

The assembly of the present invention may also comprise a closure device for enclosing at least one of the bands in the connector bar.

In use, the present invention can reduce the wall tension on one of the chambers of the heart. A yoke or collar surrounds the heart so as to provide the chamber of the heart with at least two contiguous communicating regions, such as sections of truncated ellipsoids, which have a lesser minimum radii than the chamber before restructuring. As such, the collar displaces at least two portions of the chamber wall inwardly from the unrestricted position.

BRIEF DESCRIPTION OF THE DRAWINGS

While the specification concludes with claims particularly pointing out and distinctly claiming the present invention, it is believed the same will be better understood from the following description taken in conjunction with the accompanied drawings in which:

FIG. 5 is a perspective view of a device made in accordance with the present invention;

FIG. 6 is an enlarged exploded perspective view of a portion of the assembly made in accordance with the present invention;

FIG. 7 is an enlarged perspective view of another portion of the assembly made in accordance with the present invention;

FIG. 27A is an enlarged perspective view of a connector portion of the assembly made in accordance with the present invention;

FIG. 27B is a perspective view of the assembly made in accordance with the present invention including a connector portion;

FIG. 27C is a perspective view of the embodiment of FIG. 27B, wherein the ends of the connector portion have been attached to one another;

FIG. 27D is another perspective view of the assembly made in accordance with the present invention in a generally elongated configuration;

DETAILED DESCRIPTION OF THE PREFERRED EMBODIMENTS

Figure 1:
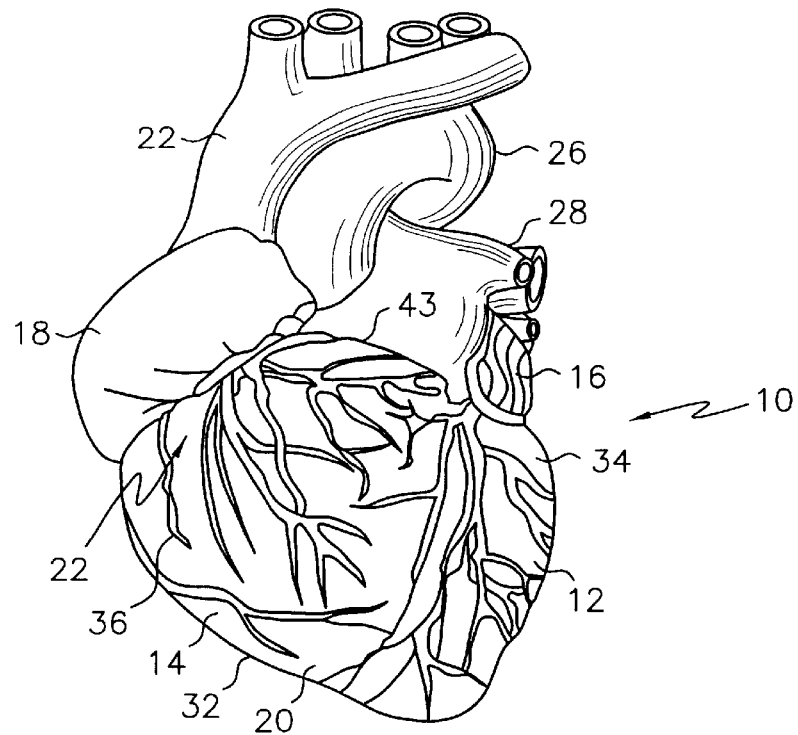
FIG. 1 is a partial frontal anterior view of an exemplar natural heart.
Figure 2:
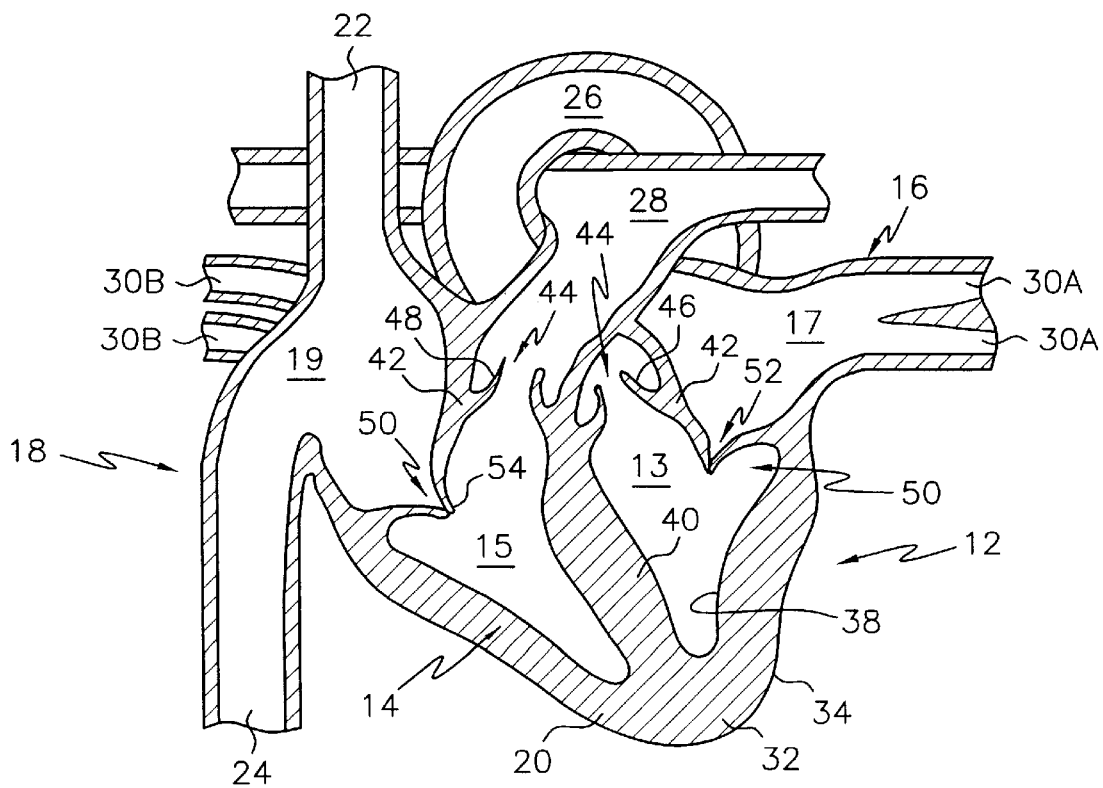
FIG. 2 is a vertical cross sectional view of an exemplar natural heart and blood vessels leading to and from the natural heart.

Referring now to the figures in detail wherein like numerals indicate the same elements throughout the views, an exemplary natural heart, generally indicated in FIGS. 1 and 2 as 10, has a lower portion comprising two chambers, namely a left ventricle 12 and a right ventricle 14, which function primarily to supply the main force that propels blood through the circulatory system, namely the pulmonary circulatory system, which propels blood to and from the lungs, and the peripheral circulatory system, which propels blood through the remainder of the body. A natural heart 10 also includes an upper portion having two chambers, a left atrium 16 and a right atrium 18, which primarily serve as an entryway to the left and right ventricles 12 and 14, respectively, and assist in moving blood into the left and right ventricles 12 or 14. The interventricular wall 40 of cardiac tissue 32 separates the left and right ventricles 12 and 14, and the atrioventricular wall 42 of cardiac tissue 32 separates the lower ventricular region from the upper atrium region.

Generally, the left and right ventricles 12 and 14, respectively, each has a cavity 13 and 15, respectively, that is in fluid communication with cavities 17 and 19, respectively, of the atria (e.g., 16 and 18) through an atrioventricular valve 50 (which are each illustrated as being in the closed position in FIG. 2). More specifically, the left ventricle cavity 13 is in fluid communication with the left atrium cavity 17 through the mitral valve 52, while the right ventricle cavity 15 is in fluid communication with the right atrium cavity 19 through the tricuspid valve 54.

Generally, the cavities of the ventricles (e.g., 13 and 15) are each in fluid communication with the circulatory system (i.e., the pulmonary and peripheral circulatory systems) through a semilunar valve 44 (which are each illustrated as being in the open position in FIG. 2). More specifically, the left ventricle cavity 13 is in fluid communication with the aorta 26 of the peripheral circulatory system through the aortic valve 46, while the right ventricle cavity 15 is in fluid communication with the pulmonary artery 28 of the pulmonary circulatory system through the pulmonic valve 48.

Blood is returned to the heart 10 through the atria (e.g., 16 and 18). More specifically, the superior vena cava 22 and inferior vena cava 24 are in fluid communication with and deliver blood, as it returns from the peripheral circulatory system, to the right atrium 18 and its cavity 19. The pulmonary veins 30 are in fluid communication with and delivers blood, as it returns from the pulmonary circulatory system, to the left atrium 16, and its cavity 17.

The heart 10 is enclosed in the thoracic cavity within a double walled sac commonly referred to as the pericardium. Its inner layer is the visceral pericardium or epicardium, and its outer layer is the parietal pericardium. The heart 10 is generally made up of, among other materials, cardiac muscle or tissue 32, which has an exterior surface commonly known as the epicardial surface 34 and an interior surface, or endocardial surface 38, that generally defines the cavities (e.g., ventricular cavities 13 and 15, respectively, and atrial cavities 17 and 19, respectively). Coronary arteries 36 on the epicardial surface 34 of the heart 10 provide blood and nourishment (e.g., oxygen) to the heart 10 and its cardiac tissue 32.

By way of a non-limiting example, the present invention will be discussed in terms of embodiments that are used to primarily assist in the restructuring or reconfiguring, and/or operation of the left ventricle chamber (e.g., 12) of the natural heart 10. However, it is noted that the present invention can also be used to assist in the restructuring or reconfiguring, and/or operation of other portions of the natural heart 10, such as either atria (16 and/or 18), and/or the right ventricle chamber (e.g., 14).

Figure 3:
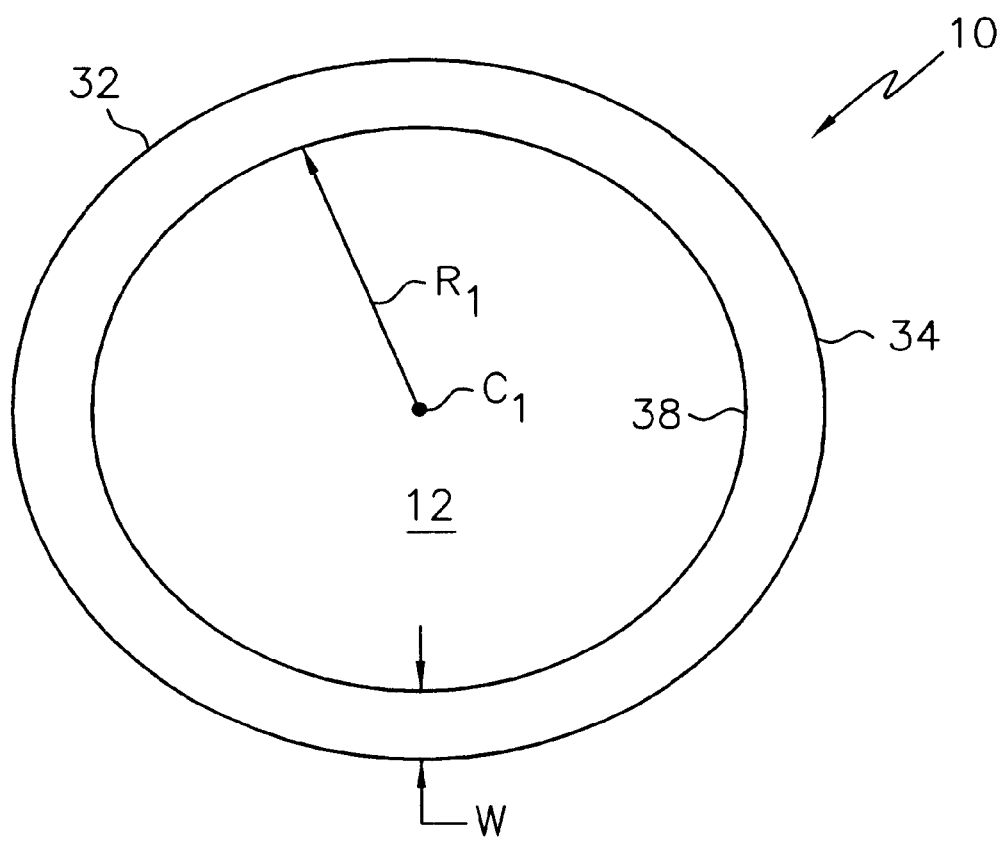
FIG. 3 is a horizontal cross sectional view of an unrestrained left ventricle of the natural heart.

Turning now to FIG. 3, each chamber of the heart 10, including the left ventricle chamber 12, is generally shaped as a hollow truncated ellipsoid having, at any circular cross-section perpendicular to its long axis, a center point "$C_1$" and a radius "$R_1$" extending from center point $C_1$ to the endocardial surface 38. The cardiac tissue 32 of the heart 10 has a thickness "w," which is generally the distance between the epicardial surface 34 and the endocardial surface 38.

Figure 4:
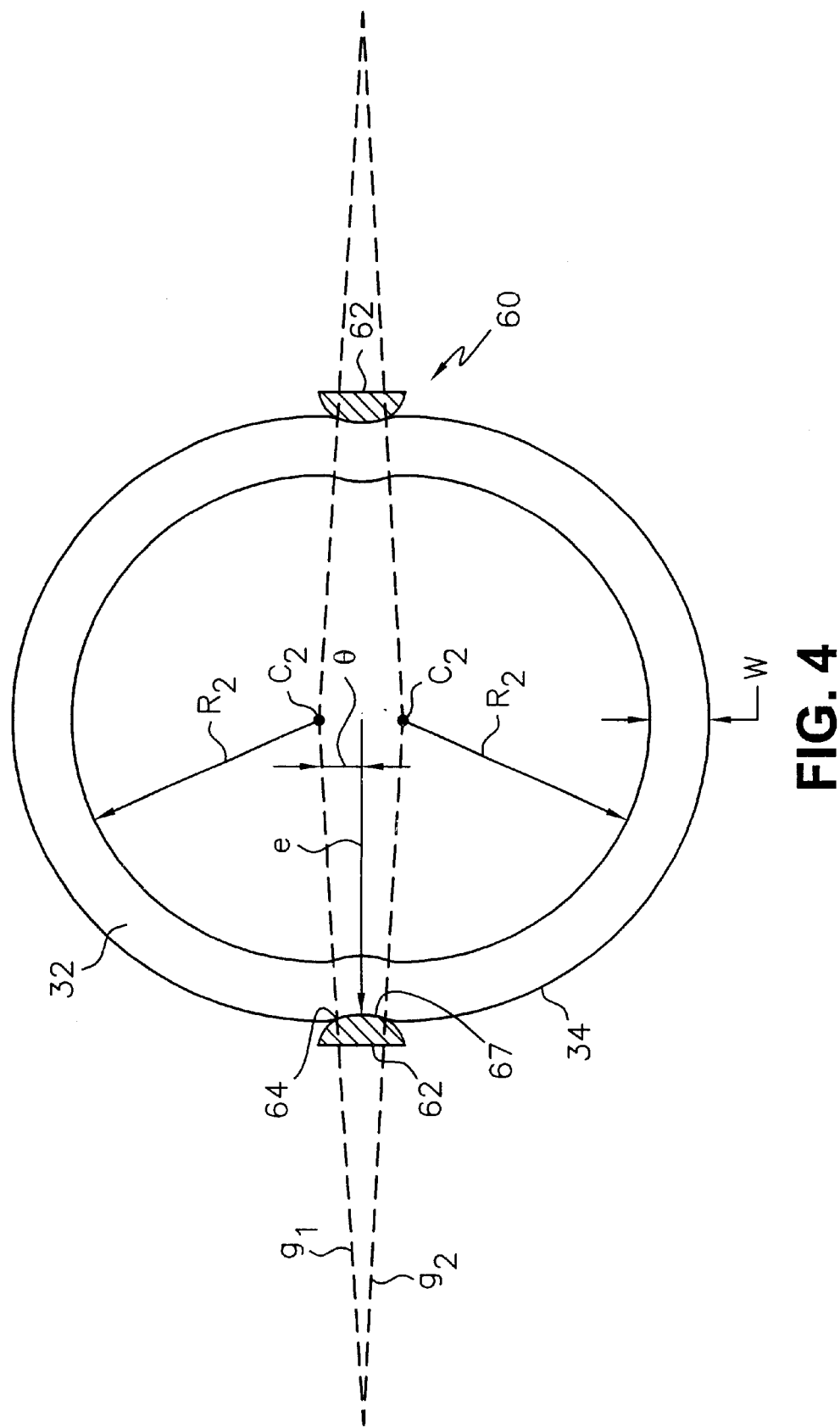
FIG. 4 is a horizontal cross sectional view of a heart restraint made in accordance with the present invention.

An assembly 60 of the present invention preferably is configured and positioned relative to the natural heart 10 to displace at least two portions of the cardiac tissue 32 inwardly (see, e.g., FIG. 4) from the unrestricted position, as exemplified in FIG. 3. By displacing portions of the cardiac tissue 32 inwardly, the shape of the chamber (e.g., the left ventricle chamber 12) of the heart 10 is generally restructured or reconfigured from a generally hollow truncated ellipsoid (see, e.g., FIG. 3) to a chamber. generally shaped as having at least two continuous communicating portions of truncated ellipsoids (see, e.g., FIG. 4). In generally reconfiguring or restructuring the heart 10 as such, each of the truncated ellipsoids has an adjusted radius "$R_2$," which is preferably shorter than radius "$R_1$."

Assembly 60 can be static or passive in that it does not actuate or pump the heart 10, but rather, displaces and holds portions of the cardiac tissue 32 in a generally predetermined fixed position as the heart 10 continues to contract (e.g., beat) and pump blood through its chambers and through the body's circulatory system. Nevertheless, assembly 60 can be configured and constructed to permit torsional deformation as the natural heart 10 beats.

Figure 10:
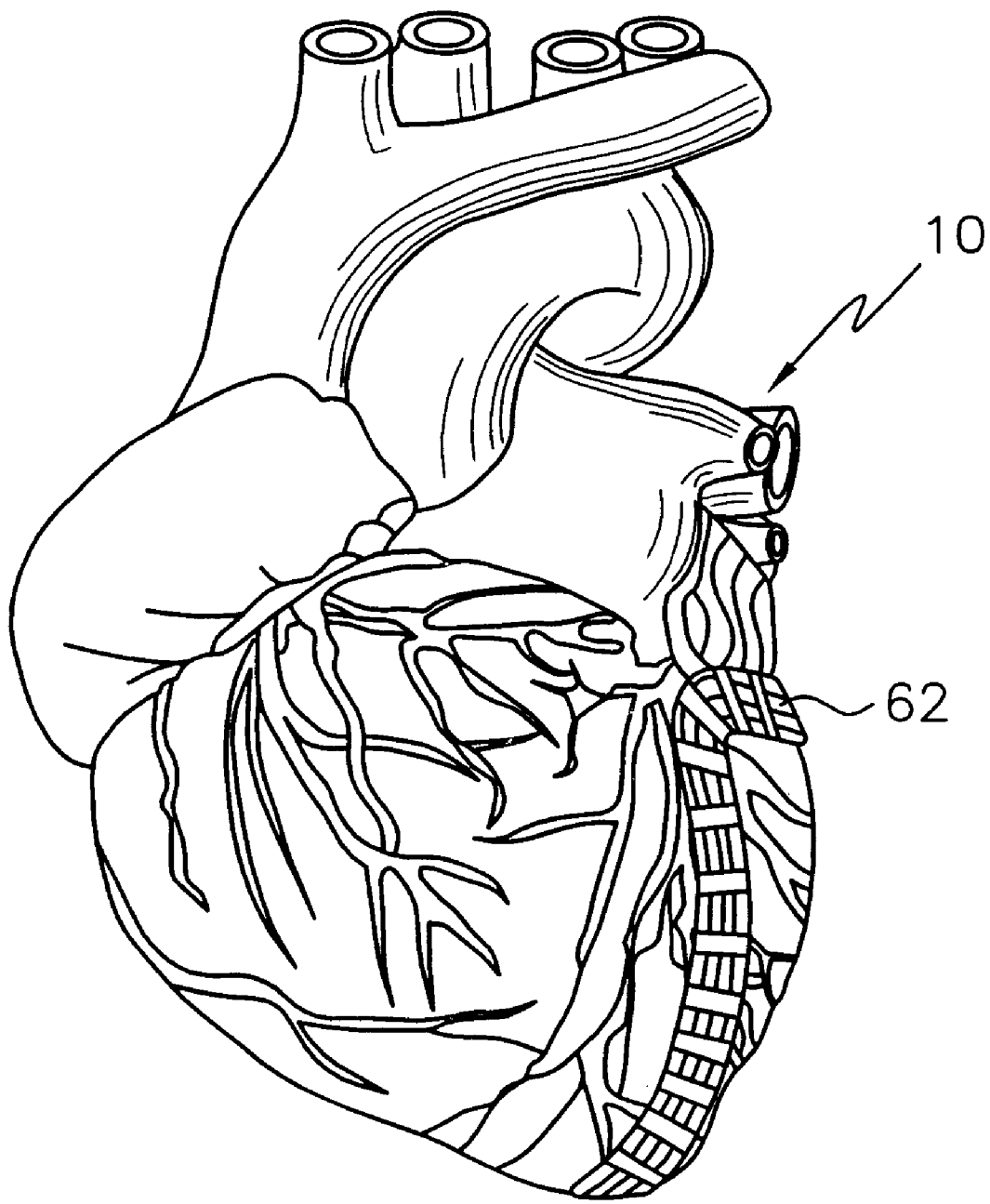
FIG. 10 is a perspective view of the assembly made in accordance with the present invention and positioned on the left ventricle.

Assembly 60 of the present invention can include a yoke or collar 62, as exemplified in FIGS. 5–7, to assist in restraining or restructuring a ventricle, such as the left ventricle chamber 12. Collar 62 can be any desired shape and preferably surrounds or encircles the heart 10, and preferably one chamber (e.g., the left ventricle chamber 12) as exemplified in FIG. 10, so as to restructure or reconfigure the left ventricle chamber 12 as having a shape approximating at least two continuous communicating portions of truncated ellipsoids (see, e.g., FIG. 4). Preferably, a portion or region 64 of the collar 62 can extend along the longitudinal plane or along the longer axis of the chamber. Suitable locations on the epicardial surface 34 for the region 64 can include the basal portion near the atrioventricular groove 43 (see, e.g., FIG. 1) and apical portion 20 of the heart 10, the anterolateral surface of the left ventricle chamber 12, or the posteromedial surface of the left ventricle chamber 12.

The collar 62 may include two or more bands (e.g., 76) configured for positioning around the heart 10. Preferably, bands 76 are circumferentially flat and may be oriented with the surface 78 being positioned generally tangent to the epicardial surface 34 of the heart 10, and having the smaller dimension, as compared with surface 80. Surface 80 is generally oriented perpendicular to the epicardial surface 34. Band 76 should be sized so as to provide for low deformation in the direction perpendicular to the epicardial surface 34 of the heart 10, but only require a low strain energy for tortial deformation as the heart 10 beats. Band 76 can have a thickness "th" across surface 78 and a width "w" across surface 80, that each varies depending on the selected material and its particular deformation characteristics. When metallic material is used with the present invention, the band 76 can have a thickness "th" across surface 78 of about 0.2 mm, and can have a width "w" across surface 80 from about 5 mm to about 12 mm, and more preferably, about 7 mm. It should be noted that the particular dimensions of each assembly 60, and of its components (e.g. collar 62 and its various portions, bands 76, etc.) will depend, as will be discussed later, according to particular anatomy, the desired application, and upon the particular size and configuration of the individual natural heart 10.

In constructing assembly 60 using bands 76, from about 2 to about 10 bands 76 may be used, and preferably about 4 bands 76 are used in the present invention. Nevertheless, the number of bands 76 may be selected depending upon the properties of the material selected for each of the bands 76, as well as the load stress required to appropriately restructure the heart chamber geometry.

Bands 76 are each preferably made of a light weight, generally rigid material that has a low bending strain under expected levels of stress so that the material has sufficient wear resistance in use while the heart 10 beats, and maintains its desired shape in use adjacent the heart 10. Illustrative examples of suitable materials which may be employed as bands 76 include any biocompatible or biomedical materials, such as metals, including titanium or stainless steel, or a suitable polymer, including polyacetal, polypropylene, rigid polyurethane or an ultra high molecular weight polyethylene, or a combination of the same.

Figure 8:
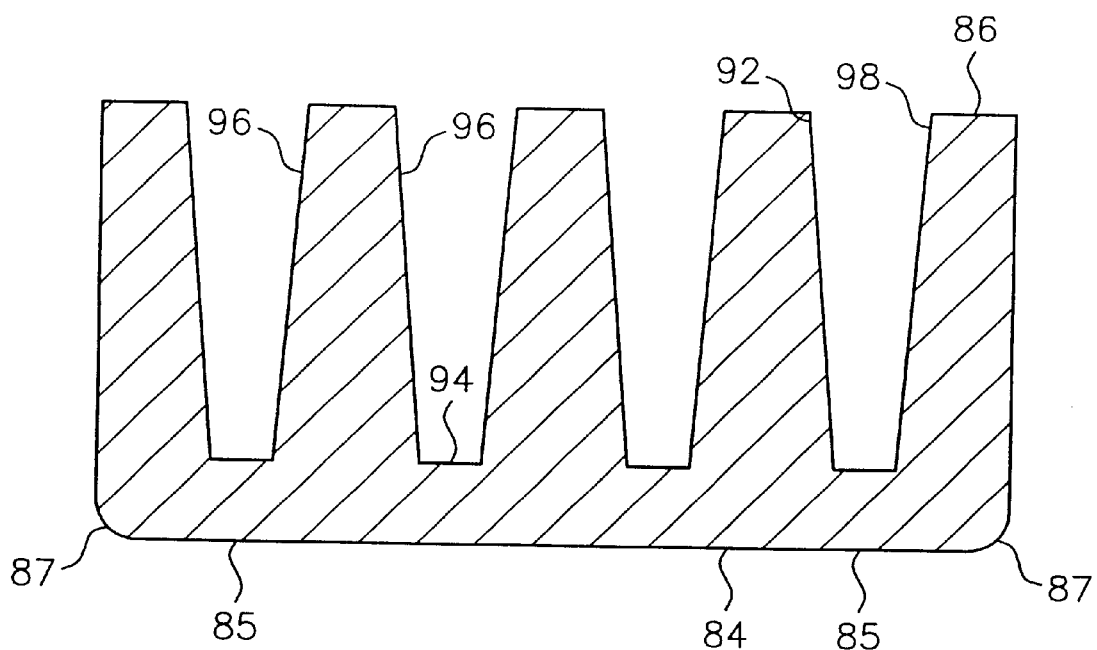
FIG. 8 is a cross sectional view of a connector of the present invention taken along line 88 in FIG. 7.

The collar 62 may preferably include a connector 82, and preferably a plurality of connectors 82 spaced along the collar 62, as exemplified best in FIG. 5. The connectors 82 can assist in maintaining the spaced relationship of the bands 76 relative to each other, and of the assembly 60 to the heart 10. Turning now to FIGS. 6–8, the connector 82 preferably has a contact or an inner surface 84, which is configured for placement adjacent or against the epicardial surface 34 of the natural heart 10. The inner surface 84 may be configured so that the epicardial surface 34 may slide along inner surface 84 during contraction and expansion of the heart 10, and to minimize damage to the epicardial surface 34, and the coronary arteries (e.g., 36). Preferably, the inner surface 84 is curved convex outwardly in a longitudinal plane (see, e.g., FIGS. 4 and 8) and has a smooth surface, and/or preferably rounded edges 87 so that collar 62 can be configured to be positioned adjacent or on the epicardial surface 34 whereby intimate contact can be established and maintained, even during the contraction or beating of the heart 10.

FIGS. 6–8 illustrate the connectors 82 as each including one or more grooves 92, which can extend inwardly from an opening 98 in the outer surface 86, and toward the contact or inner surface 84. Each groove 92 is preferably sized and configured to receive a band 76 whereby its surface 78 would be positioned adjacent the base wall 94, and its surfaces 80 preferably would be positioned adjacent sidewalls 96.

In a preferred embodiment, groove 92 should be configured to assist in allowing flexion movement of the band 76 as the heart 10 beats and moves. As best exemplified in FIGS. 6–8, grooves 92 may be tapered inwardly as the grooves 92 proceed or extend from the outer surface 86 inwardly toward the contact surface 84. In addition, grooves 92 may also be tapered inwardly as the groove extends from each of the lateral surfaces 88 inwardly (e.g., upwardly and/or downwardly), as best illustrated in FIG. 6.

Connectors 82 are each preferably made of a light weight, generally rigid material that has a low bending strain under expected levels of stress so that the material has sufficient wear resistance in use while the heart 10 beats, and maintains its desired shape in use adjacent the heart 10. Illustrative examples of suitable materials which may be employed as connectors 82 may include any biocompatible or biomedical materials, such as metals, including titanium or stainless steel, or a suitable polymer, including polyacetal or an ultra high molecular weight polyethylene, or a combination of the same.

Turning back to FIG. 6, a structure 100 can be provided so as to assist in maintaining the bands 76 in the groove 92, in use. Any structure 100 contemplated for use with assembly 60 should assist in restricting movement of the band 76 out of the groove 92 through opening 98. In one embodiment, the structure 100 may take the form of a plate 100 that can be secured or otherwise attached, and preferably releasably secured, to close off or restrict access through one or more openings 98. In addition to a plate-like structure, sutures (not shown) may also be threaded through the connector 82 to assist in restricting the movement of bands 76 through opening 98. Structure 100 is preferably made of a biocompatible or biomedical material.

Figure 11:
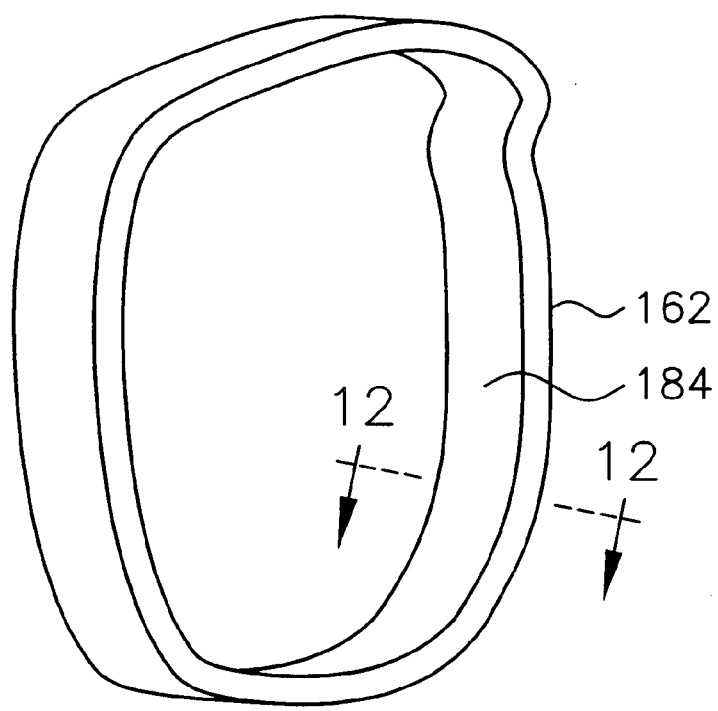
FIG. 11 is an alternative embodiment of the assembly made in accordance with the present invention.
Figure 12:
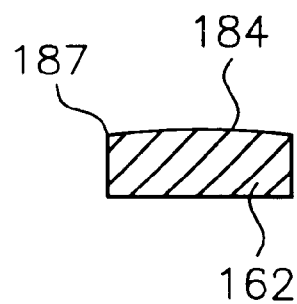
FIG. 12 is a cross sectional view of one embodiment of the collar of the present invention taken along line 12—12 in FIG. 11.

Turning now to FIGS. 11 and 12, an alternative embodiment of the present invention may include a collar or yoke 162 that provides an essentially continuous surface which contacts the epicardium surface 34 of the heart 10. In the present embodiment, collar 162 may take the form of a generally continuous yoke-like structure that is essentially rigid and/or elastic. Collar 162 preferably includes a contact or an inner surface 184, which is configured for placement adjacent or against the epicardial surface 34 of the natural heart 10. The inner surface 184 should be configured so that the epicardial surface 34 may slide along the inner surface 184 during contraction and expansion of the natural heart 10, and to minimize damage to the epicardial surface 34 and the coronary arteries (e.g., 36). Preferably, the inner surface 184 is curved convexly outwardly in a longitudinal plane and has a smooth surface, and/or preferably rounded edges 187 so that a collar 162 can be configured to be positioned adjacent or against the epicardial surface 34 whereby intimate contact can be established and maintained, even during the contraction or expansion of the natural heart 10.

The collar 162 preferably is selected from a generally rigid or tough biomedical or biocompatable material. Examples of such suitable materials which may be employed as collar 162 can include a metal, such as titanium or steel, or a polymer, such as an ultra high molecular weight polyethylene, polyurethane, polyacetal, or a polymer composite material such as carbon fiber-epoxy or fiberglass-epoxy, or a combination of the same. Moreover, the collar 162 may be covered, either partially or entirely, with a material that promotes tissue ingrowth into the collar 162, such as a soft tissue polyester fabric sheeting or polyletrafluroethyhere (PTFE).

Figure 13:
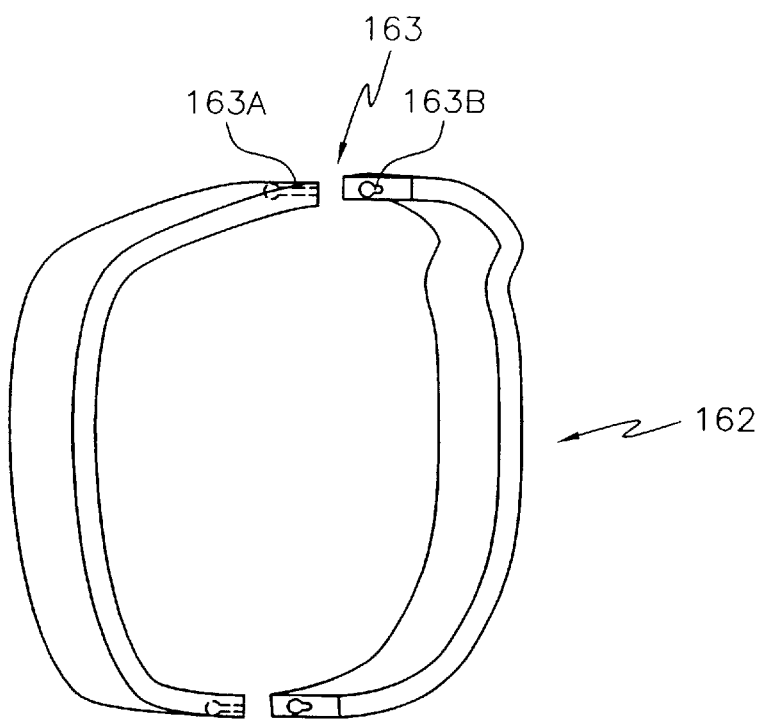
FIG. 13 is a perspective view of another alternative embodiment of the assembly made in accordance with the present invention.
Figure 14:
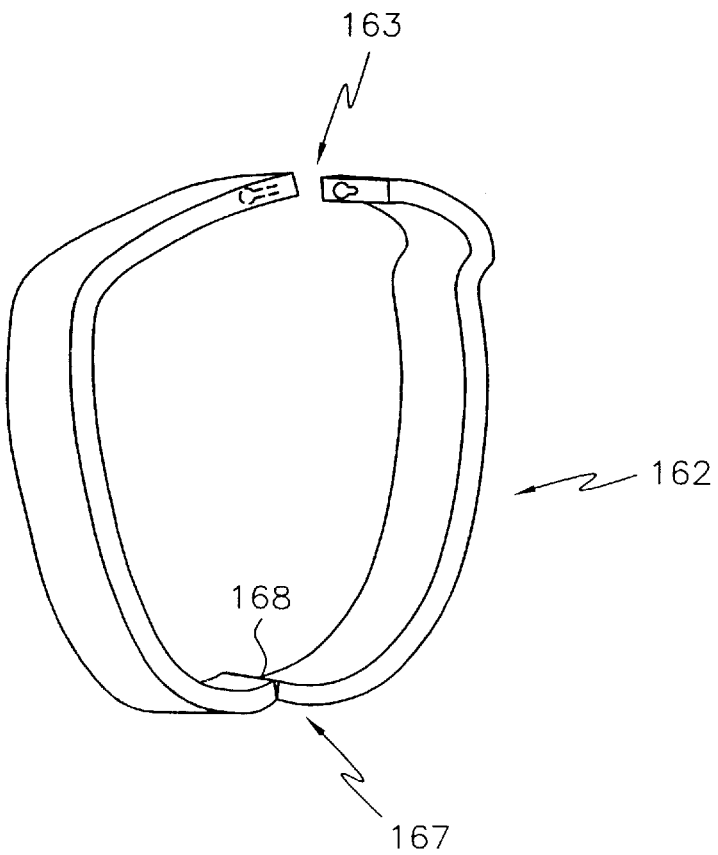
FIG. 14 is a perspective view of yet another alternative embodiment of the assembly made in accordance with the invention.

In other alternative embodiments, exemplified in FIGS. 13–14, it is contemplated that the collar 162 may include an attachment system 163 that allows the collar 162 to be placed around the heart 10, such as in between the pulmonary veins 30 (e.g., the left and right pulmonary veins 30A and 30B, respectively) near the basal portion of the heart 10 so as to reduce the possibility of lateral or medial displacement of the assembly 60, or about the lateral atrium or the atrioventricular groove region.

In one embodiment exemplified in FIG. 13, the collar 162 may include an attachment system 163 that permits the collar 162 to be separated and then reattached at two or more sites or positions along the collar 162, preferably adjacent or near the region of the collar 162 configured for placement adjacent or on the basal portion and/or apical portion 20 of the natural heart 10. While the attachment system 163 is illustrated as an interlocking pin 163B and receptacle 163A (e.g., a ball and socket-like joint), it is contemplated, and as would be appreciated by those skilled in the art, that other devices and assemblies for releasably securing the collar 162 together can be used. Examples of such devices and assemblies for attachment system 163 could include sutures, a screw and bore holes through overlapping portions of the collar 162, clamps, or a combination of these devices and assemblies.

Alternatively, as exemplified in FIG.14, the collar 162 may include an attachment system 163 at one site along the collar 162, preferably adjacent or at the portion of the collar 162 configured for placement adjacent or on the basal portion of the heart 10. This embodiment of collar 162 preferably would include a portion 167 that can either include flexible material, a pivotable section 168, or both to provide movement of the collar 162 so that the attachment assembly 163 can open, and the collar 162 can be slipped around the heart 10, such as between the left and right pulmonary veins 30A and 30B, respectively.

Figure 15:
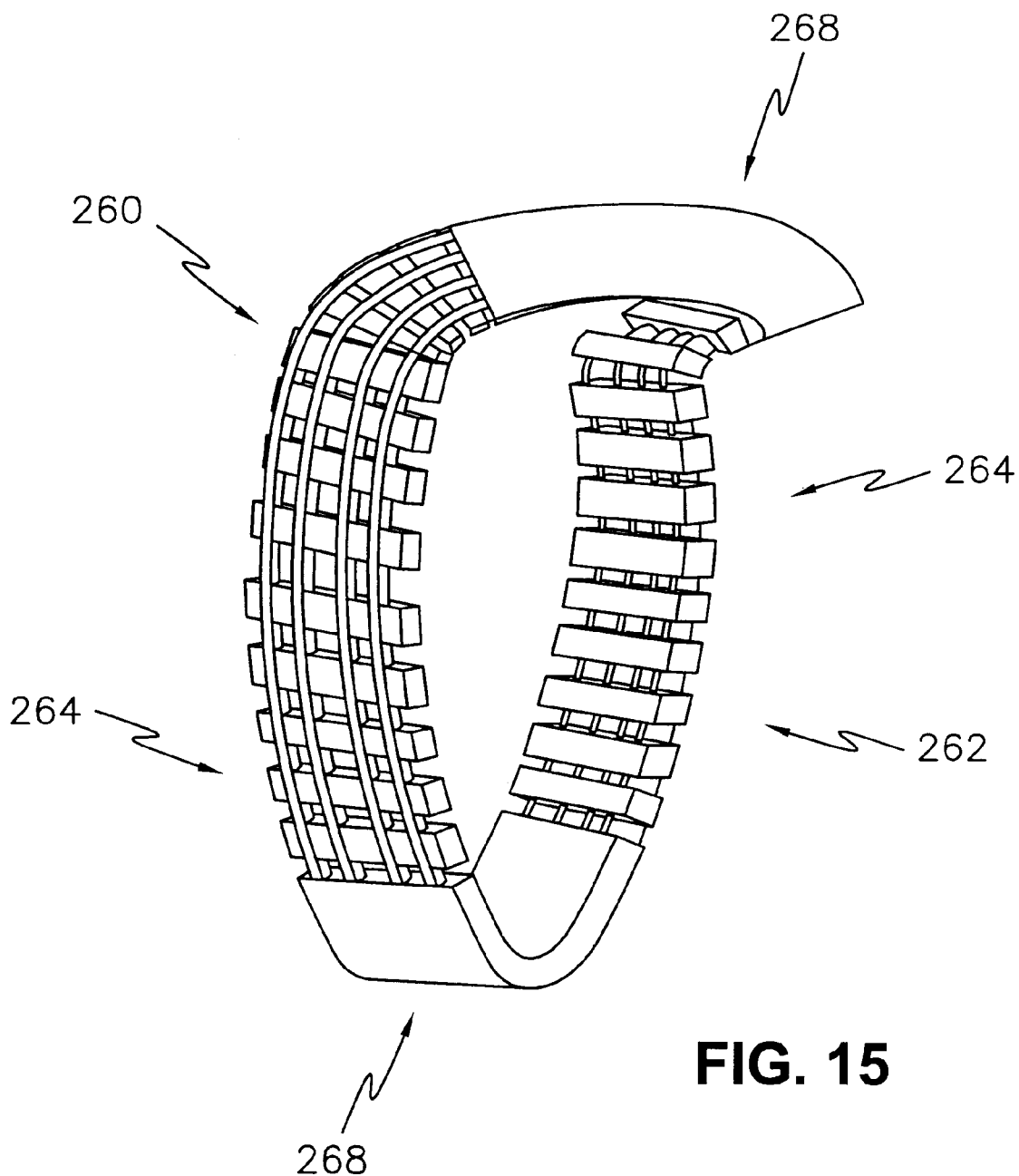
FIG. 15 is another alternative embodiment of the assembly made in accordance with the present invention.

In yet another embodiment illustrated in FIG. 15, the assembly 260 may include a collar 262 having a region 264 similar to the structure of the collar 62, exemplified above in FIGS. 4–8, and connector portions or regions 268, similar to the structure of the collar 162, discussed above, and exemplified in FIGS. 11–14.

Figure 16A:
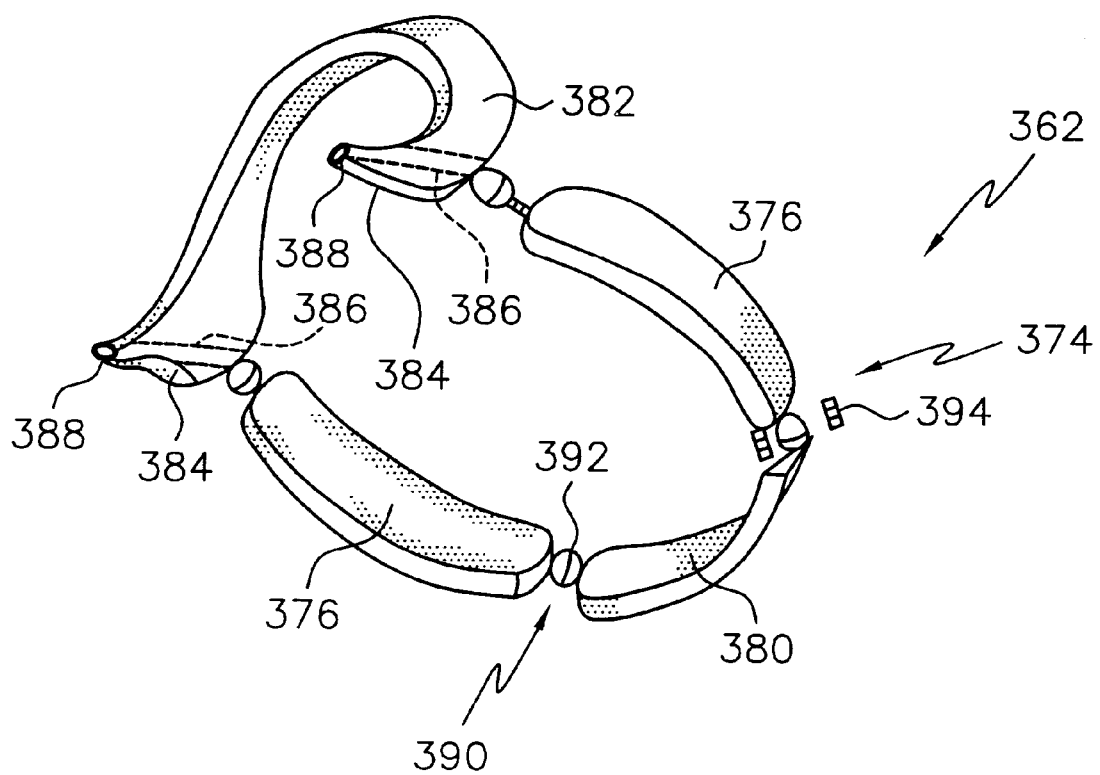
FIG. 16A is a perspective view of the assembly made in accordance with the present invention.
Figure 16B:
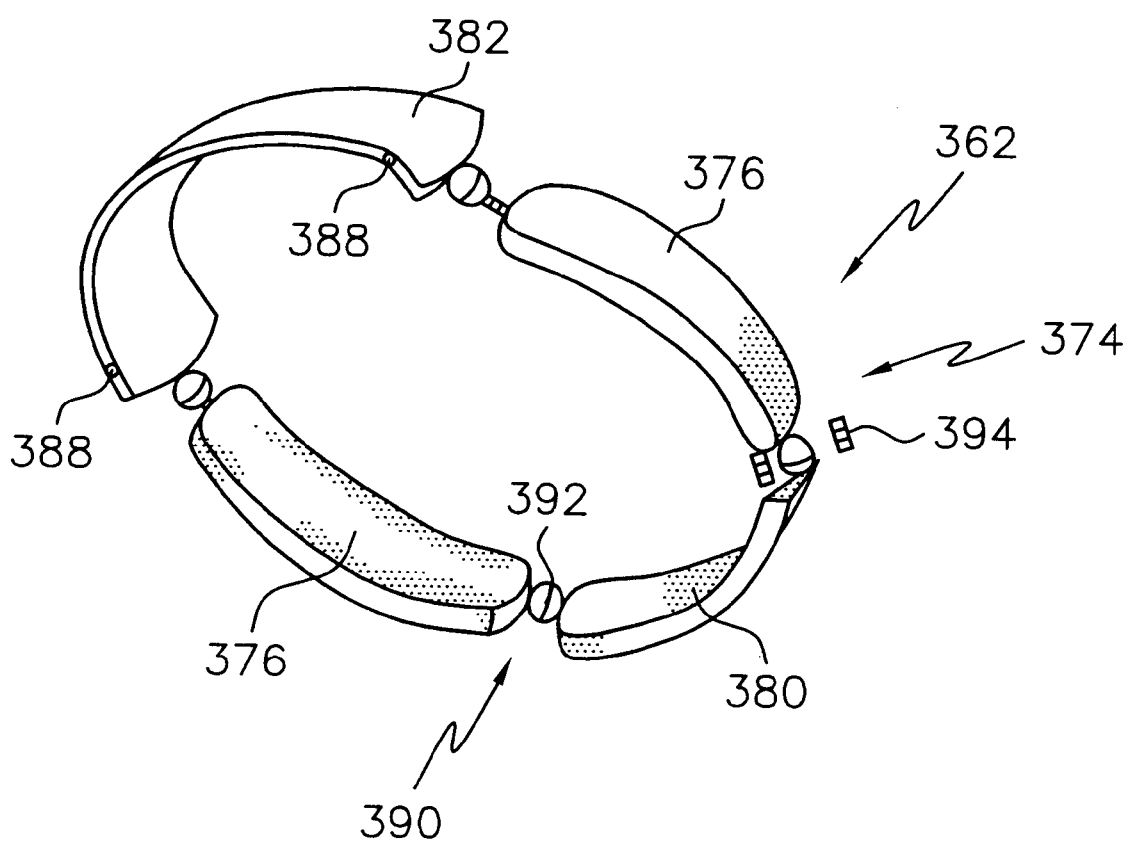
FIG. 16B is a perspective view of an alternative embodiment of the assembly made in accordance with the present invention.
Figure 17:
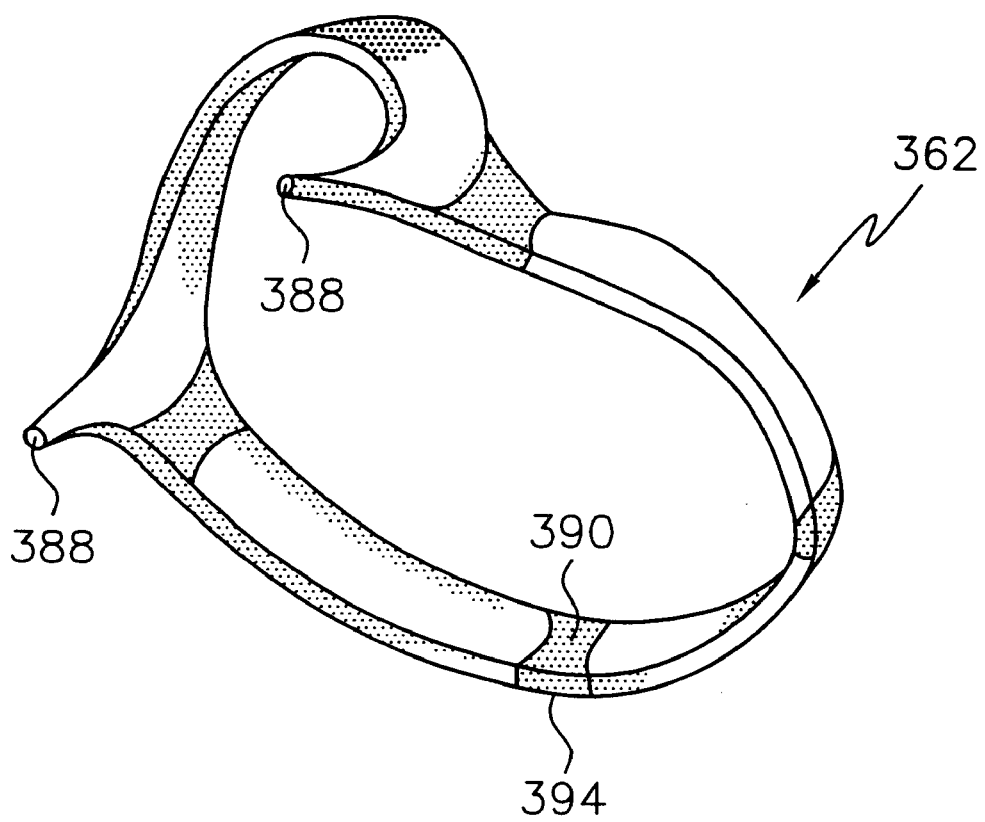
FIG. 17 is a perspective view of the assembly made in accordance with the present invention.
Figure 18:
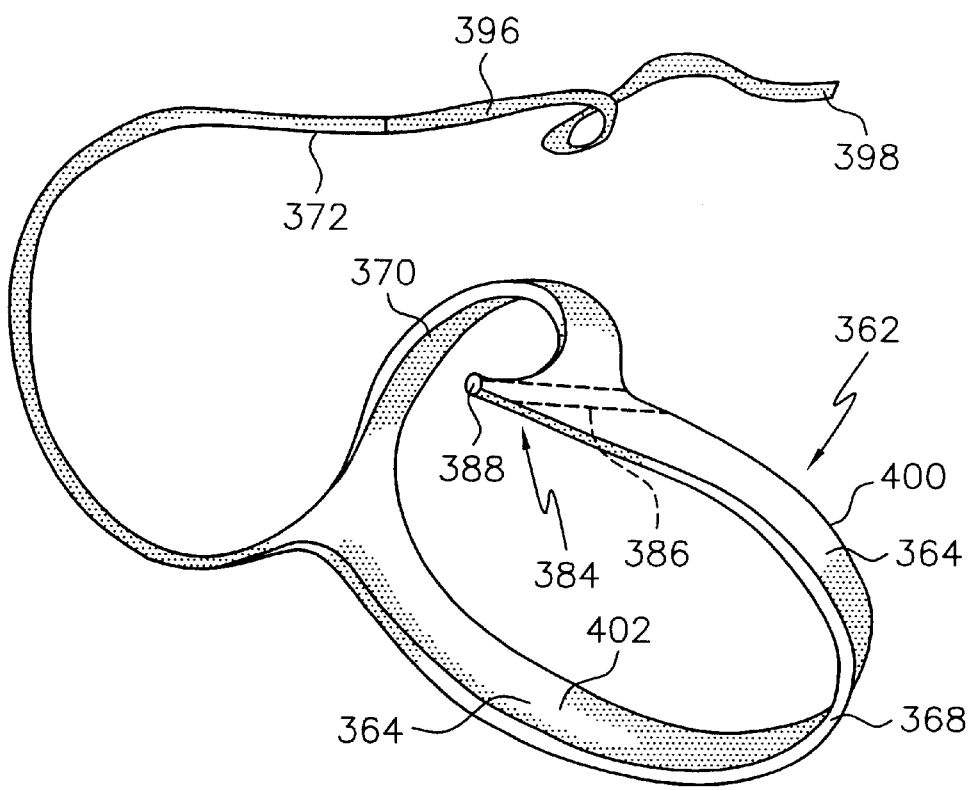
FIG. 18 is a perspective view of the assembly made in accordance with the present invention.
Figure 19:
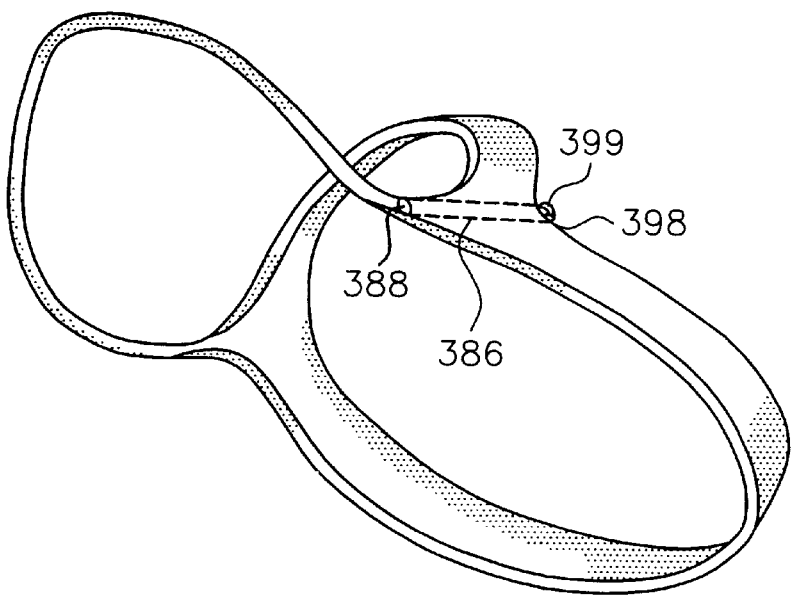
FIG. 19 is a perspective view of the assembly of FIG. 18, with the connector cord and/or portion of the collar secured to the assembly.
Figure 20:
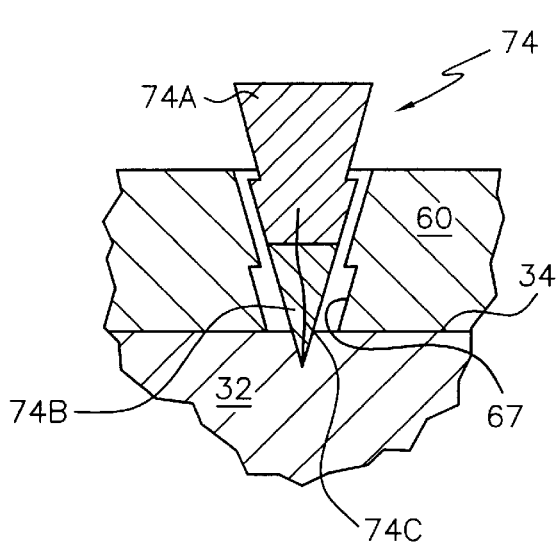
FIG. 20 is a vertical cross sectional view of one embodiment of an auxiliary fastener made in accordance with the present invention.
Figure 21:
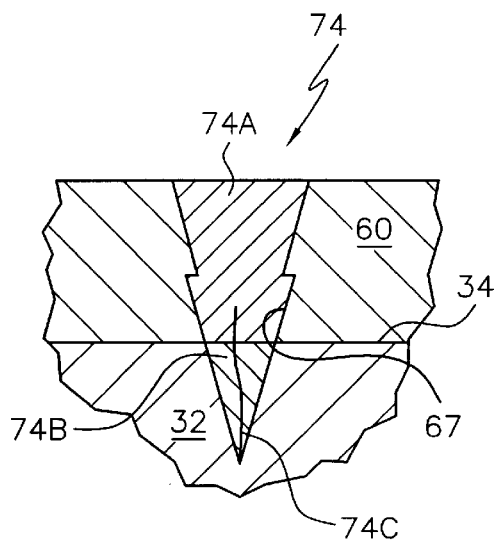
FIG. 21 is another vertical cross sectional view of the auxiliary fastener of FIG. 20 inserted into the assembly.
Figure 22:
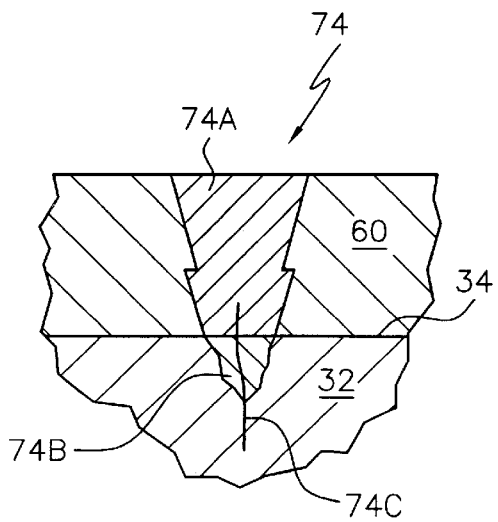
FIG. 22 is another cross sectional view of the auxiliary fastener of FIG. 20 a period of time after being inserted into position.
Figure 23:
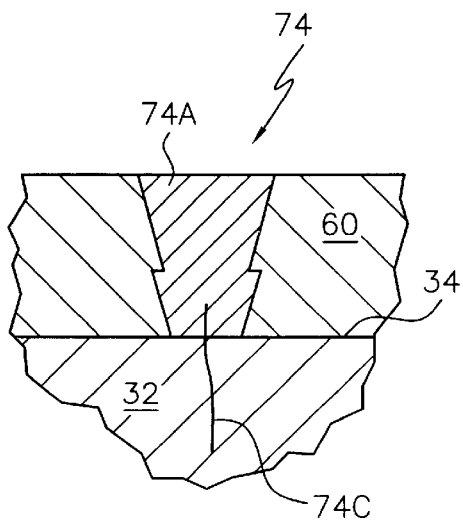
FIG. 23 is a vertical cross sectional view of the auxiliary fastener of FIG. 20 after its spike has been absorbed by tissue.

Additional embodiments of the present invention are exemplified in FIGS. 16–19, and may include a collar or yoke 362 that includes an internal frame portion 374 (see, e.g., FIGS. 16A and 16B) and an external shell or skin portion 400 (see, e.g., FIG. 18). The internal frame portion 374 is preferably configured to support the external shell portion 400, in use, and to assist in restraining or restructuring a ventricle.

Turning now to FIGS. 16A and 16B, internal frame portion 374 can include supports 376, 380, and 382, and connectors 390. Supports 376 are sized and configured to extend generally along a longitudinal plane of the longer axis of the heart 10, and preferably, are generally thin elongated panels, with a slight arc or curvature whereby they are contoured to match the epicardial surface 34.

Support 380 is preferably sized and configured to extend generally around the apical portion 20 of the heart 10, whereas support 382 is generally U-shaped and is preferably configured to extend generally around the basal portion of the heart 10. The supports 376 and 380 are preferably made of a light weight, generally rigid material that has a low bending strain under expected stress levels so that the material has sufficient wear resistance in use while the heart 10 beats, and maintains its desired shape in use adjacent the heart 10.

Support 382 is preferably more rigid as it is configured for being positioned around the basal portion of heart 10, whereby it can have a greater bending movement applied to it by the heart 10. Furthermore, it may include a metal brace encased in a polymer. Moreover, since some embodiments of the invention may be encased in external shell portion 400, the internal frame portion 374 may be selected from a group of materials that are not biocompatible, such as other metallic alloy or other polymer.

Illustrative examples of suitable materials which may be employed as supports 376, 380 and 382 can include any biocompatible or biomedical materials, such as metals, including titanium, stainless steel, or a suitable polymer, including polyacetal, polypropylene, rigid polyurethane, an ultra high molecular weight polyethylene, a fiber-reinforced polymer composite or a combination of these materials.

Figure 24:
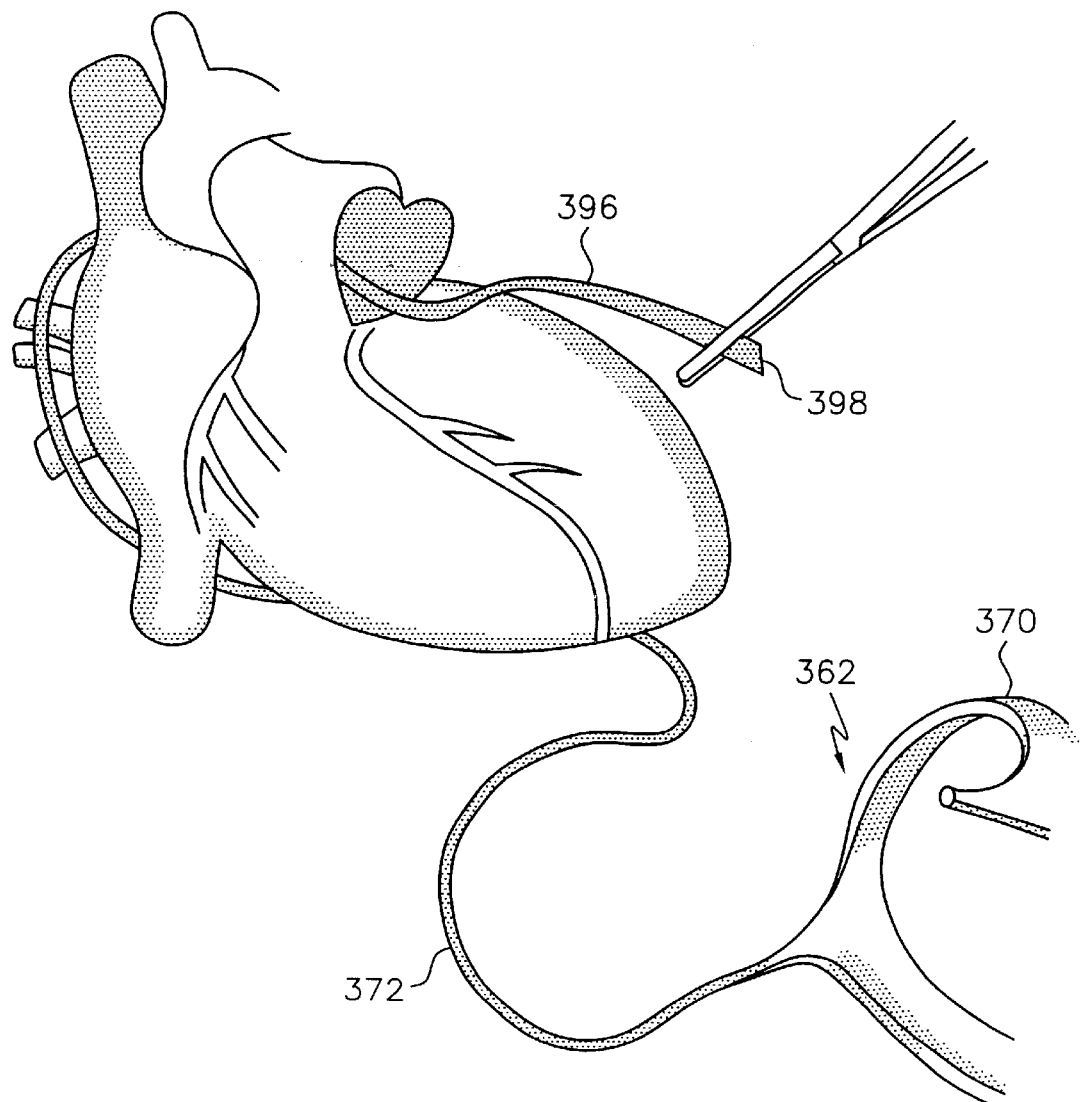
FIG. 24 is a perspective view of an exemplar heart with the assembly of the present invention being positioned on the heart.
Figure 25A:
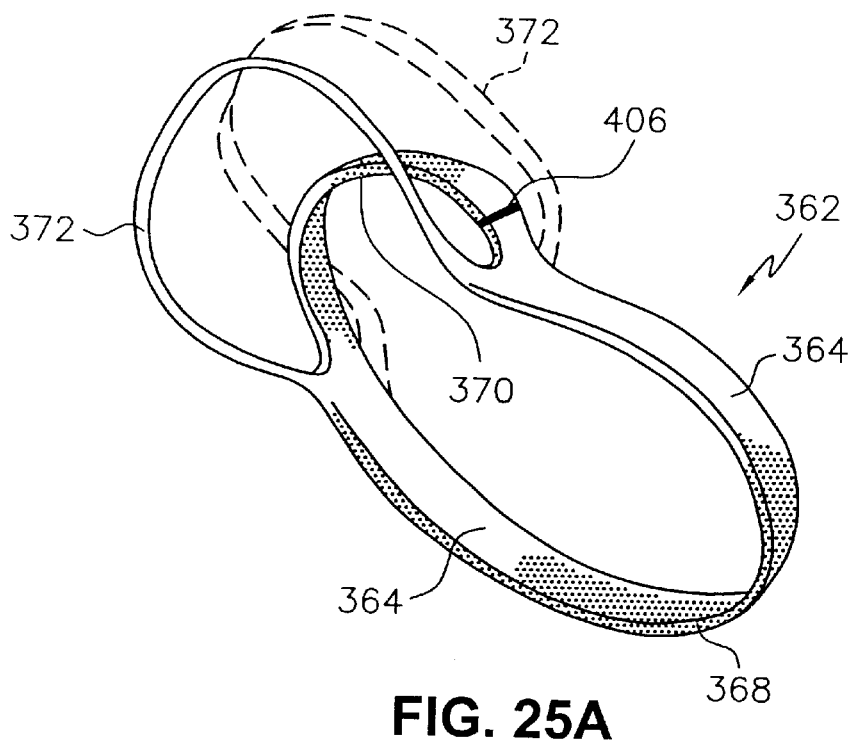
FIG. 25A is a perspective view of another embodiment of the present invention.
Figure 25B:
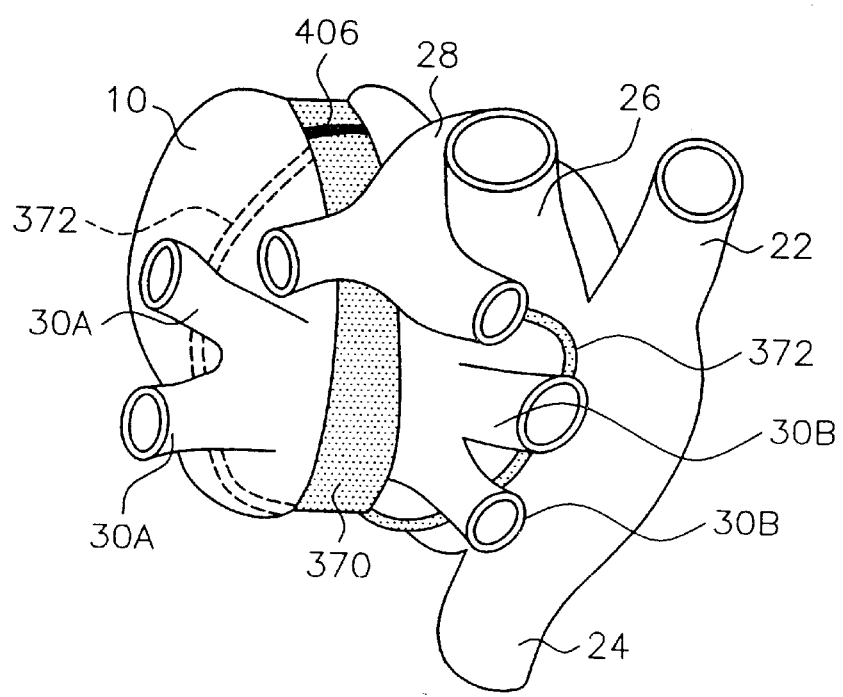
FIG. 25B is a top view of an exemplar heart with the assembly of FIG. 25A of the present invention having been positioned on the heart.
Figure 26:
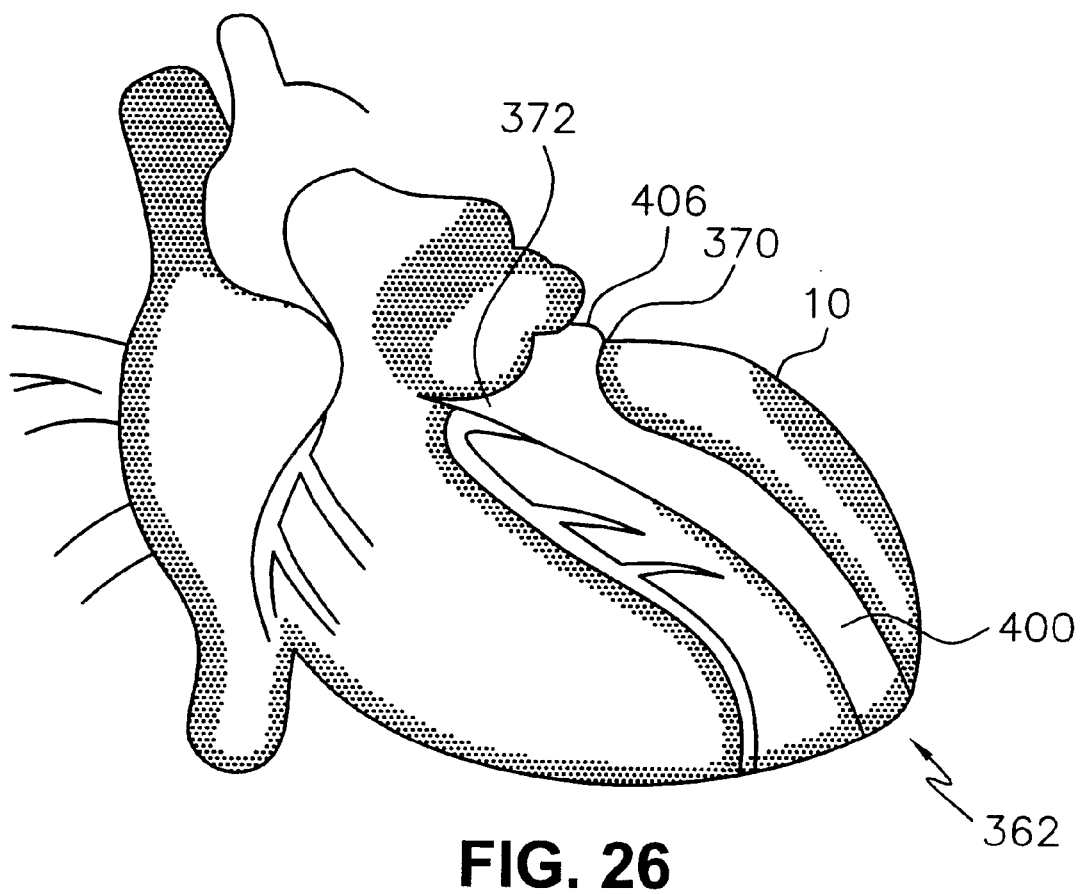
FIG. 26 is a perspective view of an exemplar heart with the assembly of the present invention having been positioned on the heart.

In the embodiment of FIG. 16A, support 382 may be configured to be positioned to the left of the left pulmonary veins 30A (as shown in FIGS. 24 and 26) and/or to the right of the right pulmonary veins 30B (simply by reversing the orientation of collar 362 from that shown in FIG. 26). Support 382 can be provided in a generally horn shaped configuration with end portions 384 at each end of support 382. As illustrated in FIGS. 16B, 25A and 25B, support 382 can also be configured to be positioned between the left and right pulmonary veins 30A and 30B, respectively, and in substantially the same plane as the other supports of collar 362.

Openings 388 are preferably provided on the surface of the support number 382, and more preferably in the end portion 384, whereby a channel 386 extends into, and preferably therethrough. Openings 388 and channels 386 are preferably sized and configured to selectively receive a connector cord 396, to assist in maintaining the position of the assembly on the heart 10, as will be discussed later herein. A similar horn shaped configuration with an end portion 384 is provided on the opposite end of support 382 in order to receive the other end of a connector cord 396.

Supports 376, 380 and/or 382 are preferably connected or joined to each other with connectors 390, as exemplified in FIGS. 16A and 16B. Connectors 390 are generally provided at or adjacent the end portions of the supports 376, 380 and/or 382. When attached to the supports 376, 380 and/or 382, connectors 390 preferably can provide for low deformation in a direction perpendicular to the epicardial surface 34 of the heart 10, and can preserve freedom for slight spontaneous systolic torsion as the heart 10 expands and contracts. Connector 390 may take the form of a ball and socket joint 392 that is made from either metal, such as steel, a polymer such as polyacetal, or a combination of steel and polymer.

Turning now to FIG. 17, the area around or adjacent connectors 390 can preferably be provided with a packing 394 to reinforce the connector 390, and to provide a generally smooth, generally crevice free surface whereby the external shell portion 400 can easily bind thereto. Moreover, where the external shell portion 400 is not used with the present invention, the packing 394 can also assist prevent tissue from becoming entangled or embedded in the connector 390. As such, tissue trauma may be reduced. Illustrated examples of suitable materials which may be employed as packing 394 may include silicon rubber or a low durometer polymer or a gel or an oil. Moreover, packing 394 may be reinforced with carbon fiber, steel, fiberglass, or another suitable reinforcing micro fiber composite materials. When packing 394 is employed in the present invention without external shell portion 400, packing 394 preferably should be selected from a suitable biomedical or biocompatible material.

Turning now to FIGS. 16A, 18, and 24, the present invention can also include one or more connector cords 396 to further assist in securing the collar 362 to the heart 10, and in maintaining its position relative to the heart 10. The end of the cord 398 is preferably joined or attached to a portion of the support 382. As exemplified in FIGS. 16A, 19, and 24, openings 388 and through channels 386 may be provided in support 382 and are preferably sized and configured to receive at least one end 398 of connector cord 396. The connector cord 396 may be attached thereto by suitable devices and techniques, such as by inserting the connector cord 396 completely through the channel 386, and providing a knot 399 at its end 398, or otherwise securing the connector cord 396 so that it does not become detached or disconnected from the support 382.

Connector cord 396 should be sized and configured to be positioned around the base portion of the heart 10. In a preferred embodiment shown in FIGS. 24 and 26, connector cord 396 should be sized and configured to pass around the heart 10 through the center along the oblique sinus between the left and right pulmonary veins 30A and 30B, respectively. Alternatively, connector cord 396 may be configured to pass around heart 10 to the right of the right pulmonary veins 30B (see, e.g., FIGS. 25A and 25B), and/or to the left of the left pulmonary veins 30A (as shown by the dashed lines in FIGS. 25A and 25B). Also, the connector cord 396 may be sized and configured to pass through the pericardial reflections behind either the inferior vena cava 24 or the superior vena cava 22, and through the free space of the transverse sinus.

Connector cord 396 is preferably made of any biocompatible flexible cord or cord-like material. Illustrative examples of suitable materials which may be employed as connector cord 396 include a braided polyester, a flexible polyurethane, insertion tape, or a combination of the same.

An external shell or skin 400 is preferably provided to encase the internal frame portion 374, and at least a portion of connector cord 396 to provide an essentially continuous surface which contacts the epicardium surface 34 of the heart 10, in use.

Supports 376 having an external shell or skin thereon are indicated at 364, support 380 having an external shell or skin thereon is indicated at 368, and support 382 having an external shell or skin thereon is indicated at 370 on the drawing figures (see FIG. 18). Also, the portion of connector cord 396 having an external shell or skin thereon is indicated at 372 in the drawing figures.

External shell or skin 400 preferably is a one piece unit which can include a contact or inner surface 402, which is generally configured for. placement adjacent or against the epicardial surface 34.

The external shell portion 400 can have a thickness of less than 80 mils, preferably can have as a thickness of up to 20 mils, and preferably can have a thickness from about 0.5 mils to about 4 mils.

Furthermore, the inner surface 402 should be configured so that the epicardial surface 34 may slide along the inner surface 402 during contraction and expansion of the heart 10, and to minimize damage to the epicardial surface 34 and the coronary arteries (see, e.g., 36 on FIG. 1). Preferably, the inner surface 402 is formed to be curved or shaped convexly outwardly in a longitudinal plane, and has a smooth surface and/or preferably rounded edges so that collar 362 can be configured to be positioned adjacent or against the epicardial surface 34 of the natural heart 10 whereby intimate contact can be established and maintained during beating of the natural heart 10. The inner surface 402 also may be textured to enhance tissue integration into and/or with the inner surface 402 and the collar 362.

External shell or skin 400 is preferably selected from a generally tough or rigid biocompatible or biomedical material. Illustrative examples of suitable materials which may be employed as external shell 400 can include a castable polyurethane solution, such as Tecoflex® by ThemoCardio Systems of Waltham, Mass. or Biomer® by Johnson & Johnson, New Brunswick, N.J. Alternatively, external shell or skin 400 may be an elastomeric material selected from a group of various rubbery materials.

In the manufacture of the collar 362, it is contemplated that the internal frame portion 374 may be assembled and one end of connector cord 396 attached thereto. The external shell portion 400 can be provided around or encase the internal frame portion 374, and at least a portion of the connector cord 396 by dipping it in a solution for the external shell portion 400, or by coating the external shell portion 400 thereon. Preferably, a stereolithography technique or other computer-driven fabrication method may be used to form and harden the external shell portion 400 around the internal frame portion 374.

Figure 9A:
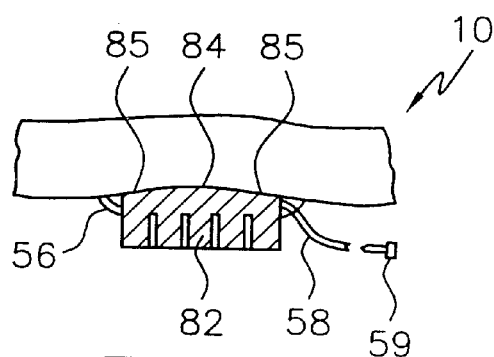
FIG. 9A is a partial horizontal cross sectional view of an assembly made in accordance with the present invention while the heart is at rest.
Figure 9B:
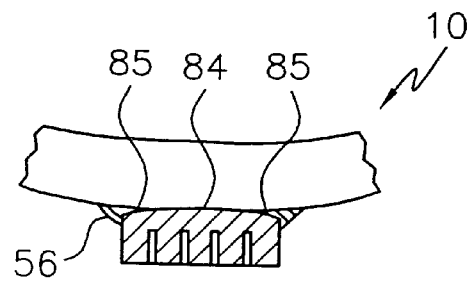
FIG. 9B is a partial horizontal cross sectional view of an assembly made in accordance with the present invention while the heart is contracting.

To assist the epicardial surface 34 in separating from any of the collars 62, 162, or 262 adjacent or at the lateral portions 85 of inner surface 84 without creating substantial negative pressure, pads can be positioned and/or interposed between the epicardial surface 34 and the inner surface of the collar. Pad 56 can be, as exemplified in FIGS. 9A and 9B, a fluid-filled or gel-filled pad or cushion. In the embodiment of FIG. 9A, pads 56 generally will occupy space laterally beyond the collar 62 and the lateral portions 85 of inner surface 84 of connectors 82 while the heart 10 is in a relaxed state. However, as the heart 10 contracts and the wall shortens (see, e.g., FIG. 9B), generally circumferentially (reducing cavity radius), the epicardial surface 34 will "peel away" from the collar 62 and the lateral portions 85 of inner surface 84 and thus, fluid or gel in the pads 56 can fill this space so that the inner surface 84 and epicardial surface 34 remain in contact and effect focal restraint whereby the chamber 12. is restructured, as detailed above.

In one embodiment, the pad 56 is a closed system. Alternatively, it is contemplated that pad 56 can be configured such that fluid and/or gel can be added or removed to enhance functionality of the device assembly of the present invention, as desired. For example, one or more lines 58 can be in fluid communication with a chamber in pad 56. Line 58 can extend from pad 56 to an injection port 59, which can be positioned subcutaneous or elsewhere, as desired, for enhanced access. As will be appreciated by those skilled in the art, fluid or gel can be injected into the injection port 59 using a standard syringe and needle, or other device, to increase the size of the pad 56 and/or the pressure within the pad 56, as desired. Alternatively, fluid or gel can be withdrawn as desired.

Alternatively, pad 56 can be a low durometer polymer such as a plastic or other material (e.g., rubber). In use, as detailed above, the material accommodates and maintains the contact between the collar 62, and more specifically its inner surface 84, and epicardial surface 34 and thus, the desired reconfiguration of the heart 10 as the heart 10 beats or deforms.

Figure 28:
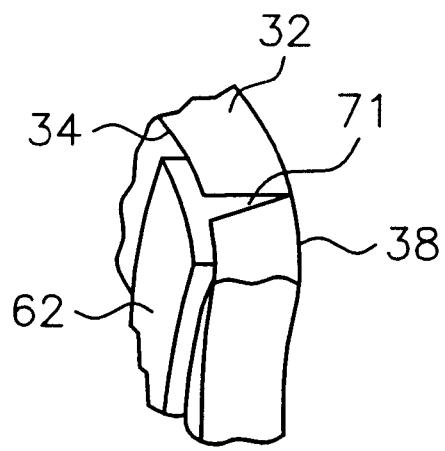
FIG. 28 illustrates another embodiment of an auxiliary fastener made in accordance with the present invention.
Figure 29:
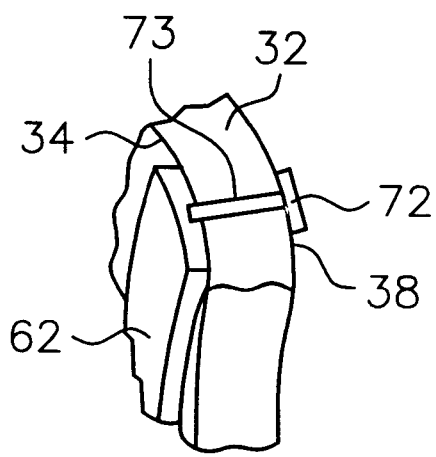
FIG. 29 illustrates still another embodiment of an auxiliary fastener made in accordance with the present invention.

To assist each assembly 60 in remaining fixed in a spatial or spaced relationship to each other and adjacent or on the epicardial surface 34, as desired, one or more auxiliary connectors may be provided (as illustrated in FIGS. 28 and 29). These auxiliary connectors can take the form of various mechanical connectors used in the industry to attach and position prosthetic devices in the body. One type of auxiliary connector is a spike shaped object or pin 71 that is configured to penetrate the epicardial surface 34 into the cardiac tissue 32. Also, the auxiliary connector(s) can take the form of a button 72 and cord 73. One end of the cord 73 can be attached or otherwise secured to the collar 62, and it can extend inwardly into and through the cardiac tissue 32. A button 72 can be attached to or adjacent the other end of the cord 73 adjacent the endocardial surface 38. Button 72 can be made of any biocompatible material, and is preferably made of a material that enhances tissue growth around the button 72 to minimize the possibility of the formation of blood clots. It is further contemplated that other surgical attachment articles and techniques can be used in accordance with the present invention, such as screws, surgical staples and the like, to assist in fastening and securing the assembly 60 in position, as desired.

Furthermore, auxiliary connector(s) can take the form of a peg 74, as exemplified in FIGS. 20–23, that can configured to be lockably received in a hole 67 positioned and/or aligned on the assembly (e.g., assembly 60) and preferably on the connectors 82 in the case of collar 62. Peg 74 generally comprises a substantially permanent portion 74A configured preferably to be snugly received in the hole 67, as discussed above. The portion 74A can be made of any suitable biomedical or biocompatible material. Suitable examples of materials for portion 74A, can include the same materials that can be used with the collar 62, as exemplified above.

At the end of the portion 74A of the peg 74, a generally rigid absorbable spike 74B is provided, which preferably is generally frustoconical shaped and tapers inwardly as the spike 74B extends away from the portion 74A. Spike 74B is sufficiently rigid so that it can pierce the tissue and then be inserted into the muscle tissue (e.g., the cardiac tissue 32). The material used for spike 74B should be a material that is absorbable by the body tissue over a period of time. Suitable materials can include a gelatin material, which can be partially denatured thermally or chemically to control solubility and the absorption rate in the tissue (e.g., 32), a polyglycol acid, or other materials, as will be appreciated by those skilled in the industry, used with absorbable surgical devices or sutures.

Within the portion 74A and spike 74B is a generally flexible extension 74C configured, for example, as a strip, coil, tube, or loop which preferably may include exposed interstices (mesh), holes, loops or other surface enhancements to promote tissue ingrowth. Extension 74C can be made from a material to enhance tissue integration therein. Suitable examples of materials for use as extension 74C can include polyester, polypropylene, and other polymers used as non-dissoluble implants.

In accordance with the teachings of the present invention, the assembly of the present invention should be so configured and positioned adjacent the heart 10 whereby the wall tension is reduced in accordance with LaPlace's theory of a chamber, which is as follows:

(Tension of wall)=$K$*(chamber pressure)*(radius of chamber)(wall thickness), wherein K is a proportionality constant.

As an illustrative example of one embodiment in accordance with the teachings of the present invention, calculations will be performed based on the following model as exemplified in FIGS. 3 and 5. It is assumed that the long axis of the left ventricle 12 of the heart 10 is 100 mm, that the equatorial or short axis of the chamber 12 is 70 mm, that the equatorial wall thickness "w" of the chamber is about 10 mm and the basal diameter of the heart 10 is 60 mm. An arbitrary slice or plane of the left ventricle 12 will be analyzed to illustrate local dimensional computations for the present invention.

Furthermore, this model will assume that the inner radius "$R_1$" (of the slice or plane) of the unrestricted heart 10 (see, e.g., FIG. 3) is about 28.982 mm and that the heart 10 has an outer radius of about 38.406 mm. As is known to those skilled in the industry, the width "w" and radius "$R_1$" can be directly obtained from high-resolution imaging, such as an echocardiogram, or preferably, by computation based on an assumed geometric model. The ratio of the restraint contact pressure on the left ventricle 12 of the device 60 to the cavity pressure can vary from 1 to about 2. This example will further assume that the allowed ratio of the restraint contact pressure on the left ventricle 12 of device 60 to the cavity pressure is to be limited to a maximum of about 1.5, which is represented by symbol K in the mathematical formulas below. Also, it is desired to achieve an altered radius "$R_2$" of the left ventricle 12 to 80% of its original radius $R_1$, and as such:

$$R_2 = 0.8 * R_1$$

$$R_2 = 0.8 * 28.982 \text{ mm}$$

$$R_2 = 23.186 \text{ mm}$$

In order to calculate the radius of curvature "g" of the inner surface 84 of collar 62 in the transverse plane, the following formula can be used:

$$g = (w + R_2) \div (K - 1)$$

$$g = (9.424 \text{ mm} + 23.186 \text{ mm}) \div (1.5 - 1)$$

$$g = (32.61 \text{ mm}) \div 0.5$$

$$g = 65.22 \text{ mm}.$$

Now that the value of radius of curvature of the inner surface 84 "g" has been calculated, the angle "θ" between the line $g_1$ (joining the center of curvature of the collar 62 with one margin, in this plane, of the contact area between inner surface 84 and the epicardial surface 34) and line $g_2$ (joining the same center of curvature with the center of the inner surface 84 in the same plane) can be calculated using the following formula:

$$\theta = (\pi/2) * [R_2 - R_1] \div (R_2 + w + g)$$

$$\theta = (\pi/2) * [28.982 \text{ mm} - 23.186 \text{ mm}] \div (28.982 \text{ mm} + 9.424 \text{ mm} + 65.22 \text{ mm})$$

$$\theta = (\pi/2) * [5.796 \text{ mm}] \div (103.636 \text{ mm})$$

$$\theta = 0.09063 \text{ radians or } 5.332 \text{ degrees}$$

Using the formula below, the distance inwardly that the heart 10 should be displaced can be calculated so that the desired restructuring can be achieved. If "e" is the distance that the center of either collar 62 is to be separated from the absolute center of a remodeled ventricle in this plane, then:

$$e = [(g + w + R_2) * \cos \theta] - g$$

$$e = [(65.22 \text{ mm} + 9.424 \text{ mm} + 23.186 \text{ mm}) * \cos 5.332 \text{ degrees}] - 65.22 \text{ mm}$$

$$e = 32.21 \text{ mm}.$$

As such, twice e or (2*e) is 64.42 mm, and this is the preferred distance separating the oppositely disposed inner surfaces 84.

Based on the calculation, the wall of the heart 10 needs to be displaced or moved inwardly about 6.20 mm from the unrestrained position to achieve the desired restructure or reconfiguration whereby wall tension is adjusted, as desired. Also, the formula 2θg can be used to calculate the desired contacting width of the inner surface 84, which is about 11.68 mm in this example.

To position the assembly 60 into a body (e.g., the thoracic cavity) and around an existing natural heart 10, a high resolution image, such as a standard echocardiogram, or other analysis of the heart 10 is preferred so that certain anatomical measurements can be electronically, preferably digitally, recorded and calculated, as detailed above. While the present application only includes one set of mathematic calculations to optimize the present invention, it is contemplated that measurements will need to be taken along several axes, planes, locations or positions along the longer axis of the chamber. Pre-surgical calculations are preferred so that the assembly 60 can be constructed, as desired, before surgery to minimize surgical time, and preferably reduce or eliminate use of a heart/lung bypass machine.

Thoracic surgery may be required to implant assembly 60. Clinically sufficient anesthesia is administered and standard cardiac monitoring is applied to the patient and then, via a sternal or lateral wall incision, the pericardial sac where the heart 10 is usually situated is opened using standard thoracic surgical procedures, which are known to those skilled in the art.

Once the thoracic cavity and pericardium are opened, the heart 10 must be narrowed or constricted so that the assembly 60 can be placed around the heart 10. In one embodiment, inflow to the heart 10 may be occluded. This can be accomplished by placing a tourniquet around either the superior and/or inferior vena cava 22 and 24, respectively, as illustrated in FIGS. 1 and 2, for a brief period of time (e.g., about 3 to 4 heartbeats) whereby the heart 10 shrinks and empties. Thereafter, the collar 62 may be slipped around the heart 10. The tourniquets can be released from occlusion around the superior and/or inferior vena cavas 22 and 24, respectively, and the heart 10 re-fills with blood.

For prolonged reduction of blood pressure by cardiac inflow occlusion, hypothermia techniques may be employed to lower body temperature to reduce the side effects that can be caused by reduced blood pressure in the circulatory system.

If an open heart procedure is employed in the present invention, circulation of blood to the natural heart 10 may be bypassed so the present invention can be inserted on and/or into the patient. If so, referring back now to FIG. 2, the superior vena cava 22, the inferior vena cava 24, and aorta 26 are cannulated. The circulatory system is connected to a cardiopulmonary bypass machine so that circulation and oxidation of the. blood are maintained during the surgical procedure. By way of example, the procedure discussed in detail will be for insertion of the present invention 60 to restructure or reconfigure the left ventricle chamber 12.

Turning now to FIGS. 4–7 and 10, an assembly 60, which may have been customized according to the anatomical measurements and calculations, is preferably positioned adjacent or against the epicardial surface 34 in predetermined locations relative to each other and relative to the chamber (e.g., left ventricle chamber 12). Assembly 60 is positioned around the heart 10 so that portions of the heart 10 are displaced or urged inwardly, as desired.

Turning now to FIGS. 18 and 24–26, collar 362, which also may have been customized according to the anatomical measurements and calculations, is preferably positioned adjacent or against the epicardial surface 34, as discussed above. The connector cord 396 may be extended around the heart 10 either to the left of the left pulmonary veins 30A (as shown by the dashed lines in FIG. 25B), to the right of the right pulmonary veins 30B (see, e.g., FIG. 25B), through the center along the oblique sinus between the left and right pulmonary veins 30A and 30B, respectively (see, e.g., FIG. 26) or any combination thereof, as desired. The connector cord 396 can be secured to the end portion 384 of support 370. For example, an end 398 of connector cord 396 may be inserted into opening 388 and through channel 386. The end of 398 may be knotted or otherwise configured so that the end 398 of connector cord 396 is not permitted to become removed or detached from the support 370.

As illustrated in FIGS. 27A–27C, a connector 406 may be provided on any portion of the collar 362, and preferably on support 370 whereby selective separation and reattachment of the first end 408 and second end 410 can be accomplished. The connector 406 can take the form of any suitable releasably looking mechanism that preferably includes a plurality of various locking positions to assist in further customizing the present invention to the heart 10, so that the degree of geometric alterations of the present invention can be adjustable, as desired.

The apparatus of the present invention can also be placed around the patient's heart 10 in a minimally invasive procedure, particularly the apparatus exemplified in FIGS. 13, 14, 25A–B and 27A–C (e.g., collars 162 and 362). As shown in FIG. 27D, collar 362 can be separated at first and second ends 408 and 410, and folded outwardly into the configuration shown in FIG. 27D (since connectors 390 will act as hinges). Thereafter, collar 362 may be inserted into the patient through a port which provides access to the pericardial sac. The port may comprise a simple incision which extends through the skin into the pericardial sac. Alternatively, the port can comprise a trocar cannula (or even the operative port of an endoscope) which has been inserted through the skin into the pericardial sac. Preferably, the port through which collar 362 is inserted is located near the apical portion 20 of the heart 10, and is about 2 cm in length.

Once collar 362 has been inserted through the port into the pericardial sac, it is manipulated into position using one or more surgical grasping devices in a manner similar to that shown in FIG. 24. In order to facilitate manipulation and proper placement of collar 362 about the heart 10, one or more trocars may be inserted into the patient so as to provide access to the pericardial sac. Preferably, these trocar(s) are inserted into the patient at locations which are higher on the chest wall than the port through which collar 362 is inserted, and an endoscope (more particularly, a thoracoscope) is inserted through at least one of the trocar cannulas. The endoscope provides operative vision within the pericardial sac (such as through a video monitor attached to the endoscope), and various. surgical grasping instruments and other necessary instruments may be inserted through the operative port of the endoscope in order to manipulate collar 362 into position around the heart. Of course these surgical instruments can also be inserted into any other trocar cannulas positioned to provide access to the pericardial sac, including the cannula (i.e., the port) through which collar 362 has been previously inserted.

Auxiliary connectors can be used to further secure the assembly 60 to the heart 10. Turning now to FIGS. 20–23, peg 74 can be inserted in the hole 67, whereby the spike 74B is piercing the epicardial surface 34 and is being inserted into the tissue (e.g., cardiac tissue 32). Peg 74 preferably locks into position once inserted (see FIG. 21), to further secure the assembly 60 in place. Over time, it is preferred that spike 74B, which has been inserted into the tissue, dissolve and be absorbed by the surrounding tissue. As the spike 74B is being absorbed, extension 74C becomes exposed to the tissue, and tissue thereby insinuates and grows into any exposed interstices, loops, holes, or other surface enhancements to promote tissue ingrowth. The peg 74 can thereafter be held in place by the tissue insinuation and growth into extension 74C, which can assist in maintaining the position of assembly 60.

Once the assembly 60 is properly positioned and secured, termination of a cardiopulmonary bypass, if used, is attempted and, if successful, the thoracotomy is closed.

Alternatively, once the thoracic cavity and pericardium are open, the collar 162 exemplified in FIGS. 13 or 14, can be placed around the heart 10, either between the pulmonary artery 28 and the superior left atrial surface or between the aorta and the pulmonary artery-28 and then across the posterior dorsal left atrial surface in between the left and right pulmonary veins 30A–B, respectively. A portion of the collar 162, preferably the posterior portion, can be placed behind the heart 10. An opening is sharply and/or bluntly developed in the leaves of the pericardium forming the anterolateral margin of the oblique sinus. Then, a hemostat can be used to place a portion of the collar 162 through the opening.

Alternatively, a detachable connector cord (see, e.g., 372 and 396) with one end attached to the portion of the collar 162, can be grasped and used to pull a portion of the collar 162 through the opening. Such placement of the collar 162 across the epicardial surface 34 of the lateral atrium or atrioventricular junction should reduce the possibility of adverse medial or lateral displacement or movement of the collar 162.

An alternative method for positioning the present invention includes removing the natural heart 10 from the patient, positioning the components of the present invention on or around the heart 10, and auto-transplanting the natural heart 10 back into the patient using standard cardiectomy and cardiac transplant techniques known in the industry.

Having shown and described the preferred embodiments to the present invention, further adaptations of the activation device for the living heart as described herein can be accomplished by appropriate modifications by one of ordinary skill in the art without departing from the scope of the present invention. For example, the present invention can be used with any one or even a plurality of the various chambers of a living heart, and also could be used with different structural embodiments to restructure the chamber. Several such potential modifications have been discussed and others will be apparent to those skilled in the art. Accordingly, the scope of the present invention should be considered in terms of the following claims and is understood not to be limited in the details, structure and operation shown and described in its specification and drawings.

I claim:

1. A device for treating a diseased heart by deforming one and only one chamber of the heart, said device comprising:
   a first member configured to be positioned adjacent an exterior surface of said chamber and to selectively deform said chamber by applying pressure to said chamber; and
   a second member coupled to said first member, wherein said second member is configured to be positioned adjacent an exterior surface of said chamber substantially opposite said first member and to restrict free movement of said chamber and to provide resistance against the pressure applied by said first member to said chamber.

2. The device according to claim 1, further comprising a cushioned portion.

3. The device according to claim 2 wherein the cushioned portion comprises a polymeric material.

4. The device according to claim 1, further comprising a pad.

5. The device according to claim 4 wherein the pad comprises a low-durometer polymer.

6. The device according to claim 4 wherein the pad comprises a cushion.

7. The device according to claim 6 wherein the cushion is gel-filled.

8. The device according to claim 6 wherein the cushion is fluid-filled.

9. The device according to claim 1 wherein said device comprises an outwardly convex configuration.

10. The device according to claim 1 further comprises an attachment system configured for releasably coupling said first and second members together.

11. The device according to claim 10 wherein the attachment system comprises a pin disposed on one of said members and a receptacle disposed on the other of said members, said pin and receptacle being releasably attachable to one another.

12. The device according to claim 1 wherein said first member is configured to be disposed adjacent an anterolateral surface of a left ventricle.

13. The device according to claim 1 wherein said first member is configured to be disposed adjacent a posteromedial surface of a left ventricle.

14. The device according to claim 1 wherein said chamber is a ventricle.

15. The device according to claim 1 wherein said chamber is an atrium.

16. The device according to claim 1, further comprising at least one deformable portion permitting the device to torsionally deform as the heart beats.

17. The device according to claim 1 wherein said first and second members are integrally coupled to form a monolithic device.

18. A device for treating a diseased heart by deforming one and only one chamber of the heart, said device having an outwardly convex configuration and comprising:
- a first member configured to be positioned adjacent an exterior surface of said chamber and to selectively deform said chamber by applying pressure to said chamber;
- a second member coupled to said first member, wherein said second member is configured to be positioned adjacent an exterior surface of said chamber substantially opposite said first member and to restrict free movement of said chamber and to provide resistance against the pressure applied by said first member to said chamber; and
- an attachment system configured for releasably coupling said first and second members together.

19. The device according to claim 18 wherein the attachment system comprises a pin disposed on one of said members and a receptacle disposed on the other of said members, said pin and receptacle being releasably attachable to one another.

20. The device according to claim 18 wherein said first member is configured to be disposed adjacent an anterolateral surface of a left ventricle.

21. The device according to claim 18 wherein said first member is configured to be disposed adjacent a posteromedial surface of a left ventricle.

22. The device according to claim 18 wherein said chamber is a ventricle.

23. The device according to claim 18 wherein said chamber is an atrium.

24. The device according to claim 18, further comprising at least one deformable portion permitting the device to torsionally deform as the heart beats.

25. A method of treating a diseased heart by deforming one and only one chamber of the heart, said chamber having an outer wall, said method comprising the steps of:
- providing a device having a first member configured to overlie a first portion of said outer wall of said chamber and a second member attached to said first member, said second member configured to engage a second portion of said outer wall of said chamber substantially opposite said first portion, and
- causing said first member to press inwardly on said outer wall to form an indentation in said outer wall, while said second member restricts free movement of said chamber and resists the pressure applied by said first member to said chamber.

26. The method of claim 25, further comprising the step of temporarily restricting blood inflow into the heart before causing said first member to press inwardly on said outer wall.

27. The method of claim 25, wherein a plurality of first members are attached to said second member and each of said plurality of first members is configured to press inwardly on different selected portions of an outer wall of one chamber of said heart, each forming indentations in said wall and reducing the volume of said chamber.

* * * * *